US011384391B2

(12) United States Patent
Ju et al.

(10) Patent No.: US 11,384,391 B2
(45) Date of Patent: Jul. 12, 2022

(54) FLOURESCENE ENERGY TRANSFER-BASED SINGLE MOLECULE/ENSEMBLE DNA SEQUENCING BY SYNTHESIS

(71) Applicant: THE TRUSTEES OF COLUMBIA UNIVERSITY IN THE CITY OF NEW YORK, New York, NY (US)

(72) Inventors: Jingyue Ju, Englewood Cliffs, NJ (US); Shiv Kumar, Belle Mead, NJ (US); James J. Russo, New York, NY (US); Steffen Jockusch, New York, NY (US); Zengmin Li, Flushing, NY (US); Xiaoxu Li, New York, NY (US); Sergey M. Kalachikov, Bronx, NY (US); Irina Morozova, Bronx, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 483 days.

(21) Appl. No.: 16/091,442

(22) PCT Filed: Apr. 4, 2017

(86) PCT No.: PCT/US2017/025848
§ 371 (c)(1),
(2) Date: Oct. 4, 2018

(87) PCT Pub. No.: WO2017/176677
PCT Pub. Date: Oct. 12, 2017

(65) Prior Publication Data
US 2019/0153527 A1    May 23, 2019

Related U.S. Application Data

(60) Provisional application No. 62/317,810, filed on Apr. 4, 2016.

(51) Int. Cl.
| | | |
|---|---|---|
| *C12Q 1/68* | (2018.01) | |
| *C07H 19/10* | (2006.01) | |
| *C07H 19/20* | (2006.01) | |
| *C12Q 1/6869* | (2018.01) | |

(52) U.S. Cl.
CPC ......... *C12Q 1/6869* (2013.01); *C07H 19/10* (2013.01); *C07H 19/20* (2013.01)

(58) Field of Classification Search
CPC ....... C12Q 1/6869; C07H 19/10; C07H 19/20
See application file for complete search history.

(56) References Cited

U.S. PATENT DOCUMENTS

| | | | |
|---|---|---|---|
| 8,314,216 | B2 | 11/2012 | Hardin et al. |
| 8,603,741 | B2 | 12/2013 | Emig et al. |
| 8,927,212 | B2 | 1/2015 | Kong et al. |
| 2010/0167277 | A1 | 7/2010 | Harper |
| 2013/0264207 | A1 | 10/2013 | Ju et al. |
| 2014/0206550 | A1 | 7/2014 | Bjornson et al. |
| 2014/0234853 | A1 | 8/2014 | Vander Horn et al. |

FOREIGN PATENT DOCUMENTS

WO    WO 2006/035207 A2    4/2006

OTHER PUBLICATIONS

Shao et al. "Emulsion PCR: A High Efficient Way of PCR Amplification of Random DNA Libraries in Aptamer Selection" PLoS ONE, Sep. 2011, vol. 6, Issue 9, e24910, pp. 1-7. (Year: 2011).*
International Search Report dated Aug. 7, 2017 in connection with PCT International Application No. PCT/US2017/025850.
Written Opinion of the International Searching Authority dated Aug. 7, 2017 in connection with PCT International Application No. PCT/US2017/025850.
Communication forwarding Extended European Search Report, issued by the European Patent Office dated Jan. 8, 2020, concerning counterpart European Patent Application No. 17779618.2.
Communication pursuant to Article 94(3), dated Mar. 30, 2021 by the European Patent Office in connection with European Application No. EP 17779618.2-1118.
Second Office Action, dated Mar. 16, 2021 by the China National Intellectual Property Administration in connection with Chinese Application No. 201780034768.2.
Response to Second Office Action, filed May 28, 2021 to the China National Intellectual Property Administration in connection with Chinese Application No. 201780034768.2 in Chinese, and English draft thereof.

* cited by examiner

*Primary Examiner* — Jezia Riley
(74) *Attorney, Agent, or Firm* — Gary J. Gershik

(57) ABSTRACT

This invention provides nucleotide analogues each of which comprises a tag comprising one or more Forster resonance energy transfer (FRET) acceptor fluorophores, a nucleotide polymerase having one or more FRET donor fluorophores, and methods for sequencing single-stranded.

20 Claims, 8 Drawing Sheets

BASE = Adenine, Guanine, Thymine, Cytosine, Uracil or derivatives thereof
n = 0-6
Acceptor dye = Organic fluorophore, such as cyanine dyes (e.g. Cy5), rhodamine dyes (e.g. ROX), or others
R' and Cleavable linker = Allyl (-CH$_2$-CH=CH$_2$), MOM (-CH$_2$OCH$_3$), AZM (-CH$_2$N$_3$), -CH$_2$S-S-alkyl and 2-Nitrobenzyl Example of 3'-O blocked nucleotides labled with combinatorial fluorescence energy transfer tag at the terminal phosphate.

BASE: Adenine, Guanine, Thymine, Cytosine, Uracil or derivatives thereof
n = 0-6
m = 1-8
R' = Allyl (-CH$_2$-CH=CH$_2$), MOM (-CH$_2$OCH$_3$), AZM (-CH$_2$N$_3$), -CH$_2$S-S-alkyl and 2-Nitrobenzyl
R = Alkyl

FLOURESCENE ENERGY TRANSFER-BASED SINGLE MOLECULE/ENSEMBLE DNA SEQUENCING BY SYNTHESIS

CROSS-REFERENCE TO RELATED APPLICATIONS

This application is a § 371 national stage of PCT International Application No. PCT/US2017/025848, filed Apr. 4, 2017, claiming the benefit of U.S. Provisional Application No. 62/317,810, filed Apr. 4, 2016, the contents of each of which are hereby incorporated by reference into the application.

Throughout this application, certain publications are referenced, the by authors and publication year. Full citations for these Publications may be found immediately preceding the claims. The disclosures of these publications in their entireties are hereby incorporated by reference into this application in order to describe more fully the state of the art to which this invention relates.

BACKGROUND OF THE INVENTION

High throughput DNA sequencing is essential to a broad array of genomic studies, such as whole genome and metagenome sequencing, expression profiling of mRNAs and miRNAs, discovery of alternatively spliced and polyadenylated transcripts, histone and chromatin changes involved in epigenetic events, and identification of binding sites for transcription factors and RNA binding proteins. Sequencing of individual human genomes is especially appealing, with its potentially unlimited but as yet unachieved promise for personalized medicine.

Given the ever-growing importance of high throughput DNA sequencing for biological and anthropological research, agriculture and medicine, there is a need for sequencing technologies that are low-cost and rapid on the one hand, and have high sensitivity and accuracy on the other. Sequencing by Synthesis (SBS) has driven much of the "next generation" sequencing technology, allowing the field to approach the $100,000 Genome [Fuller et al. 2009, Hawkins et al. 2010, Morozova et al. 2009, and Park 2009]. With further improvements in nucleotide incorporation detection methods, SBS could be an engine that drives third-generation platforms leading to the reality of the "$1,000 Genome".

Current commercial next-generation sequencing platforms have certainly made substantial inroads in this direction, with the current cost of sequencing a human genome at high draft coverage significantly below $10,000 [Fuller et al. 2009, Hawkins et al. 2010, Morozova et al. 2009, and Metzker 2010]. Expression studies (e.g. using RNA-Seq) and epigenetic studies (e.g. using Methyl-Seq, ChIP-Seq), among many others, have also benefited greatly from these platforms [Ozsolak et al. 2011, Varley et al. 2010, and Park 2009]. Nonetheless, these costs are still prohibitive for most laboratories and for clinical applications.

All of the current approaches have one or more additional limitations: biased coverage of GC-rich or AT-rich portions of genomes; inability to accurately sequence through homopolymer stretches; inability to directly sequence RNA; high reagent costs; difficulty in sequencing beyond 200 or so nucleotides resulting in difficulty in de novo assembly of previously unsequenced genomes; insufficient throughput due to ceiling on number of possible reads per run.

To overcome these obstacles, a number of third-generation sequencing platforms have appeared on the market, or are in development. All of these have issues with accuracy and most have limited throughput.

The underlying photophysical principle for this SBS method is based on Förster resonance energy transfer (FRET), where the energy of electronic excited states of a donor molecule is transferred to an acceptor molecule via non-radiative dipole-dipole interactions. As a result, the luminescence of the donor molecule is quenched and fluorescence of the acceptor molecule is observed. The occurrence and efficiency of FRET depends on various parameters, such as the distance (<10 nm) between the donor and acceptor as well as the spectral overlap between the donor luminescence and acceptor absorption spectra (Hung et al 1996, Turro et al 2010). In the past FRET has been used for Sanger sequencing (Ju et al 1995). In the current application, this has been extend to SBS.

SUMMARY OF THE INVENTION

A method for determining the identity of a nucleotide in a single-stranded DNA comprising:

a) contacting a composition comprising a single-stranded DNA having a primer hybridized to a portion thereof, with one or more non-catalytic metal ions, a nucleotide polymerase, and a nucleotide analogue having the structure:

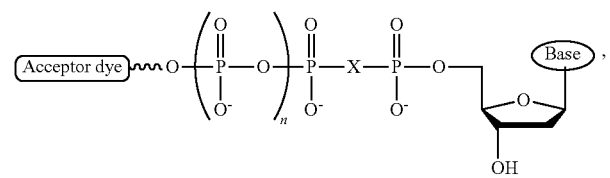

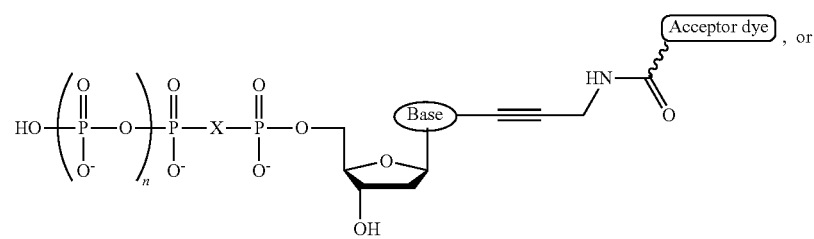

-continued

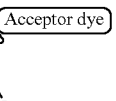
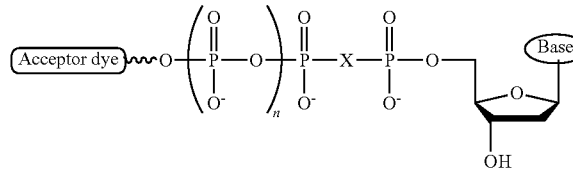

wherein the base is A, C, G, T, or U, or analogues thereof, wherein X is $CH_2$, NH, CHF, or $CF_2$, wherein n is 0, 1, 2, 3, or 4, wherein the acceptor dye is one or more fluorophores, and wherein X prevents a nucleotide polymerase from hydrolyzing the bond between the α and β phosphates, under conditions permitting the nucleotide polymerase to form a ternary complex with the single-stranded DNA, primer, and the nucleotide analogue if the nucleotide analogue has a base that is complementary to a nucleotide residue of the single-stranded DNA which is immediately 5' to a nucleoside residue of the single-stranded DNA hybridized to the 3' terminal nucleotide residue of the primer, wherein the DNA polymerase has attached, incorporated, and/or conjugated fluorescence donor molecules, wherein the donor molecules are Förster Resonance Energy Transfer (FRET) donors, and the acceptor dyes on the nucleotide analogue are corresponding FRET acceptors, wherein if the base of the nucleotide analogue is not complementary to the nucleotide residue of the single-stranded DNA which is immediately 5' to the nucleoside residue of the single-stranded DNA hybridized to the 3' terminal nucleotide residue of the primer, iteratively repeating the contacting with a different nucleotide analogue until a nucleotide analogue is complementary to the nucleotide residue of the single-stranded DNA which is immediately 5' to the nucleoside residue of the single-stranded DNA hybridized to the 3' terminal nucleotide residue of the primer, thus forming a ternary complex, with the proviso that (i) the type of base on each nucleotide analogue is different from the type of base on each of the other nucleotide analogues, and (ii) the acceptor dyes of each nucleotide analogue fluorophore has a predetermined fluorescent wavelength emission;

b) excite the DNA polymerase donor fluorescent molecules using an appropriate spectral emission, thereby causing the corresponding FRET acceptors, which are the acceptor dye organic fluorophores attached to nucleotide analogue in the ternary complex, to generate the predetermined fluorescent wavelength emission, and thereby determine the identity of the nucleotide analogue.

This invention also provides a method for determining the nucleotide sequence of a single-stranded DNA comprising:

a) contacting the single-stranded DNA, wherein the single-stranded DNA has a primer hybridized to a portion thereof, with a non-catalytic metal ion, a DNA polymerase, and a nucleotide analogue having the structure:

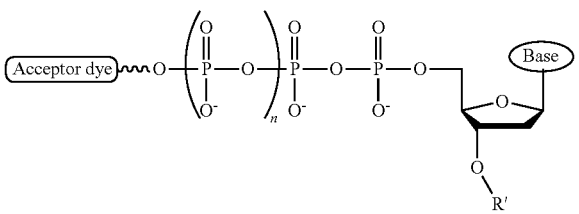

wherein the base is A, G, C, T, or U, or analogues thereof, wherein n is 0, 1, 2, 3, or 4, wherein the acceptor dye is one or more organic fluorophores, wherein R' is a cleavable linker bound to a blocking moiety, and wherein cleaving the linker results in a 3'-OH, under conditions permitting the DNA polymerase to form a ternary complex with the single-stranded DNA, primer, and a nucleotide analogue wherein the nucleotide analogue has a base that is complementary to a nucleotide residue of the single-stranded DNA which is immediately 5' to a nucleoside residue of the single-stranded DNA hybridized to the 3' terminal nucleotide residue of the primer, and wherein the nucleotide polymerase has attached or incorporated fluorescence donor molecules, wherein the DNA polymerase has attached, incorporated, and/or conjugated fluorescence donor molecules, wherein the donor molecules are Förster Resonance Energy Transfer (FRET) donors, and the acceptor dyes and the acceptor dyes on the nucleotide analogue are corresponding FRET acceptors;

b) exciting the DNA polymerase donor fluorescent molecules using an appropriate spectral emission, thereby causing the corresponding FRET acceptors, which are the acceptor dye organic fluorophores attached to the nucleotide analogue in the ternary complex, to generate the unique predetermined fluorescent wavelength emission, and thereby determine the identity of the nucleotide analogue;

c) contact the ternary complex with catalytic metal ions permitting the DNA polymerase to incorporate the nucleotide analogue into the primer;

d) cleave the linker bound to the blocking moiety of the incorporated analogue thereby resulting in a 3'-OH;

e) iteratively performing steps a) through d) for each nucleotide residue of the single-stranded DNA to be sequenced so as to thereby determine the sequence of the single-stranded DNA.

This invention also provides a real-time method for determining the nucleotide sequence of a single-stranded DNA comprising:

a) contacting a composition comprising a single-stranded DNA which has a primer hybridized to a portion thereof, a nucleotide polymerase, and four nucleotide analogues having the structure:

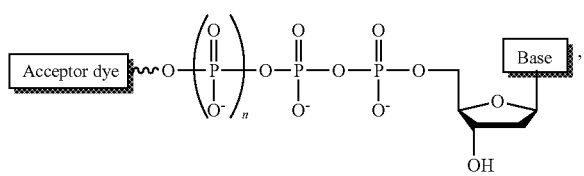

wherein the base is A, G, C, T, or U, or analogues thereof, wherein n is 0, 1, 2, 3, or 4, wherein the acceptor dye is one or more fluorophores, under conditions permitting the nucleotide polymerase to incorporate a nucleotide analogue when the nucleotide analogue has a base that is complementary to a nucleotide residue of the single-stranded DNA which is immediately 5' to a nucleotide residue of the single-stranded DNA hybridized to the 3' terminal nucleotide residue of the primer, and wherein the nucleotide polymerase has attached or incorporated fluorescence donor molecules, wherein the nucleotide polymerase has attached, incorporated, and/or conjugated fluorescence donor molecules, wherein the donor molecules are Förster Resonance Energy Transfer (FRET) donors, and the acceptor dyes and the acceptor dyes on the nucleotide analogue are corresponding FRET acceptors;

b) exciting the nucleotide polymerase fluorescence donor molecules using an appropriate spectral emission, thereby causing the corresponding FRET acceptors attached to the nucleotide analogues, to generate the unique predetermined fluorescent wavelength emission, and thereby determine the identity of the nucleotide analogue;

c) iteratively performing steps a) through b) for each nucleotide residue of the single-stranded DNA to be sequenced so as to thereby determine the sequence of the single-stranded DNA.

DETAILED DESCRIPTION OF THE INVENTION

Figure 1:
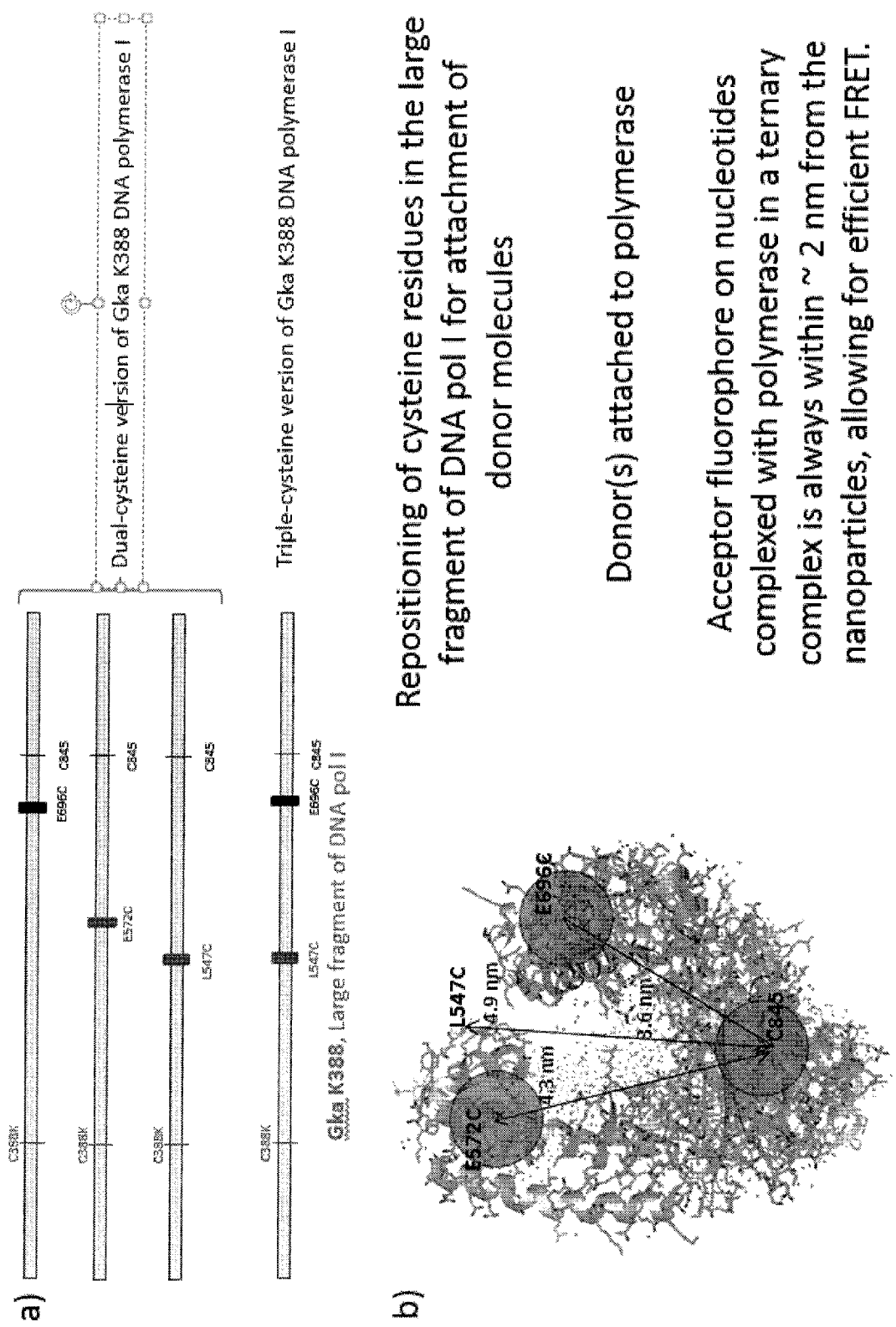
FIG. 1: Formation of a ternary complex by the polymerase carrying energy donors near the active site with nucleotides labeled with acceptor fluorophores coupled with primed template enables efficient energy transfer from donor to acceptor that will be detected for sequencing. To achieve this, repositioning of cysteine residues in the large fragment of DNA pol I for attachment of these donors was performed. a) Amino acid positions for attachment of energy donors such as organic fluorophores, quantum dots or metal complexes to the large fragment DNA polymerase I from *Geobacillus kaustophilus* were selected outside the enzyme's catalytic center. The cysteine at position C388 in a wild-type enzyme was substituted with lysine and the amino acids in the designated positions were in turn substituted with cysteines by means of recombinant DNA techniques and can now be used for attachment to donors along with C845. b) Distances of 4 to 5 nm between the wild type C845 and the various substituted designated cysteine positions ensure that donor will be close to the active center of the enzyme. In this way they will be able to transfer energy to the acceptor dye(s) on the incoming nucleotide. The donor-acceptor distance will be ~2-4 nm which is favorable for FRET.

This invention provides a nucleoside polyphosphate analogue having the structure:

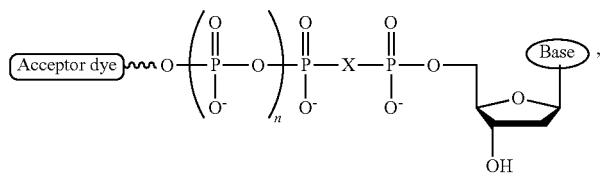

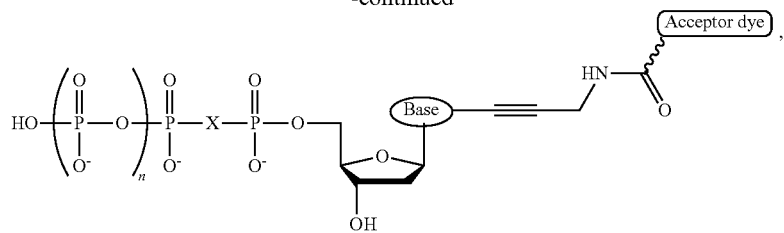

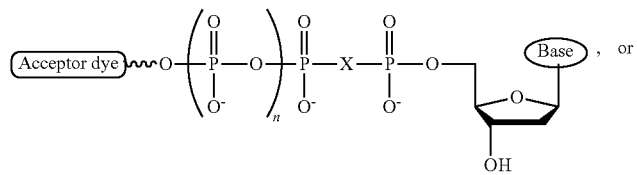

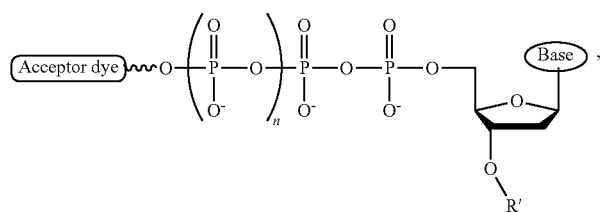

wherein the base is adenine, guanine, cytosine, uracil, thymine, or a derivative thereof, wherein X is $CH_2$, NH, CHF, or $CF_2$, wherein n is 0, 1, 2, 3, or 4, wherein each acceptor dye is a fluorophore, and where R' is H or a cleavable linker bound to a blocking moiety.

In another embodiment the acceptor dye is 1, 2, or 3 fluorophores. In another embodiment the fluorophores are organic fluorophores. In a further embodiment the organic fluorophores are separated by a separation distance that prevents the organic fluorophores from significantly quenching each other. In yet a further embodiment the organic fluorophores are one or more of a cyanine dye, a rhodamine dye, fluorescein, acridine, coumarin, Texas Red dye, BODIPY, GFP, rhodol, ROX, resorfuin, Alexa Flour, Tokyo Green, N,N,N',N'-tetramethyl-6-carboxyrhodamine, or any derivative thereof.

In another embodiment the cleavable linker is photocleavable or chemically cleavable. In another embodiment the cleavable linker is any one of an allyl group, alkyl group, carbonyl group, Sieber linkers, indole, disulfide, dithiomethyl group, azidomethyl group, nitrobenzyl group.

This invention also provides method for determining the identity of a nucleotide in a single-stranded DNA comprising:

a) contacting a composition comprising a single-stranded DNA having a primer hybridized to a portion thereof, a nucleotide polymerase, and a nucleotide analogue having the structure:

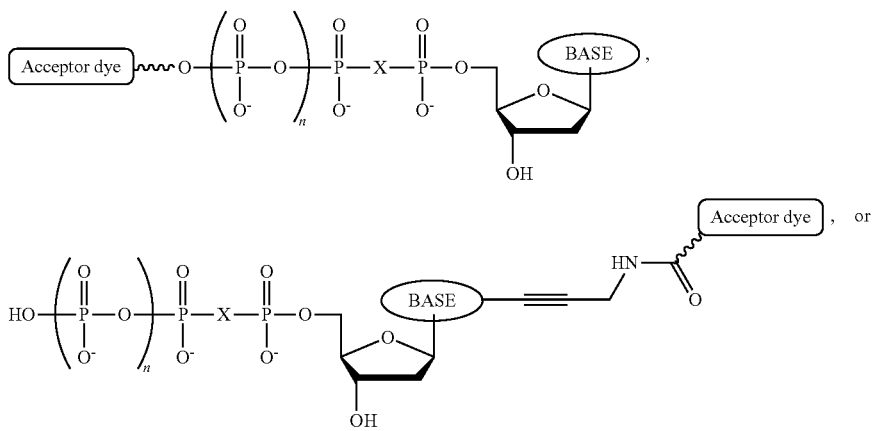

-continued

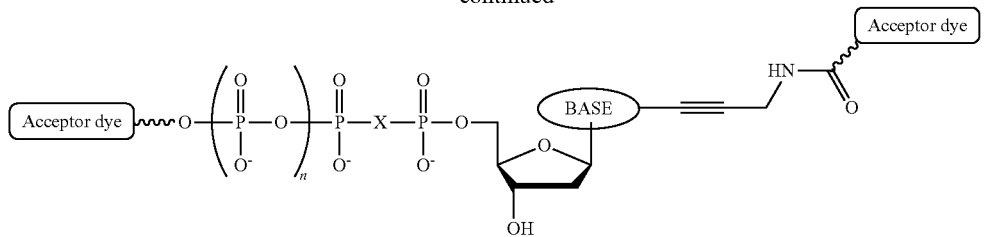

wherein the base is A, C, G, T, or U, or analogues thereof, wherein X is $CH_2$, NH, CHF, or $CF_2$, wherein n is 0, 1, 2, 3, or 4, wherein the acceptor dye is one or more fluorophores, and wherein X prevents a nucleotide polymerase from hydrolyzing the bond between the α and β phosphates, under conditions permitting the nucleotide polymerase to form a ternary complex with the single-stranded DNA, primer, and the nucleotide analogue if the nucleotide analogue has a base that is complementary to a nucleotide residue of the single-stranded DNA which is immediately 5' to a nucleoside residue of the single-stranded DNA hybridized to the 3' terminal nucleotide residue of the primer, wherein the DNA polymerase has attached, incorporated, and/or conjugated fluorescence donor molecules, wherein the donor molecules are Förster Resonance Energy Transfer (FRET) donors, and the acceptor dyes on the nucleotide analogue are corresponding FRET acceptors, wherein if the base of the nucleotide analogue is not complementary to the nucleotide residue of the single-stranded DNA which is immediately 5' to the nucleoside residue of the single-stranded DNA hybridized to the 3' terminal nucleotide residue of the primer, iteratively repeating the contacting with a different nucleotide analogue until a nucleotide analogue is complementary to the nucleotide residue of the single-stranded DNA which is immediately 5' to the nucleoside residue of the single-stranded DNA hybridized to the 3' terminal nucleotide residue of the primer, thus forming a ternary complex, with the proviso that (i) the type of base on each nucleotide analogue is different from the type of base on each of the other nucleotide analogues, and (ii) the acceptor dyes of each nucleotide analogue fluorophore has a predetermined fluorescent wavelength emission;

b) exciting the DNA polymerase donor fluorescent molecules using an appropriate spectral emission, thereby causing the corresponding FRET acceptors, which are the acceptor dye organic fluorophores attached to nucleotide analogue in the ternary complex, to generate the predetermined fluorescent wavelength emission, and thereby determine the identity of the nucleotide analogue.

This invention also provides a method for determining the nucleotide sequence of a single-stranded DNA comprising:

a) contacting the single-stranded DNA which has a primer hybridized to a portion thereof, a nucleotide polymerase, and a nucleotide analogue having the structure:

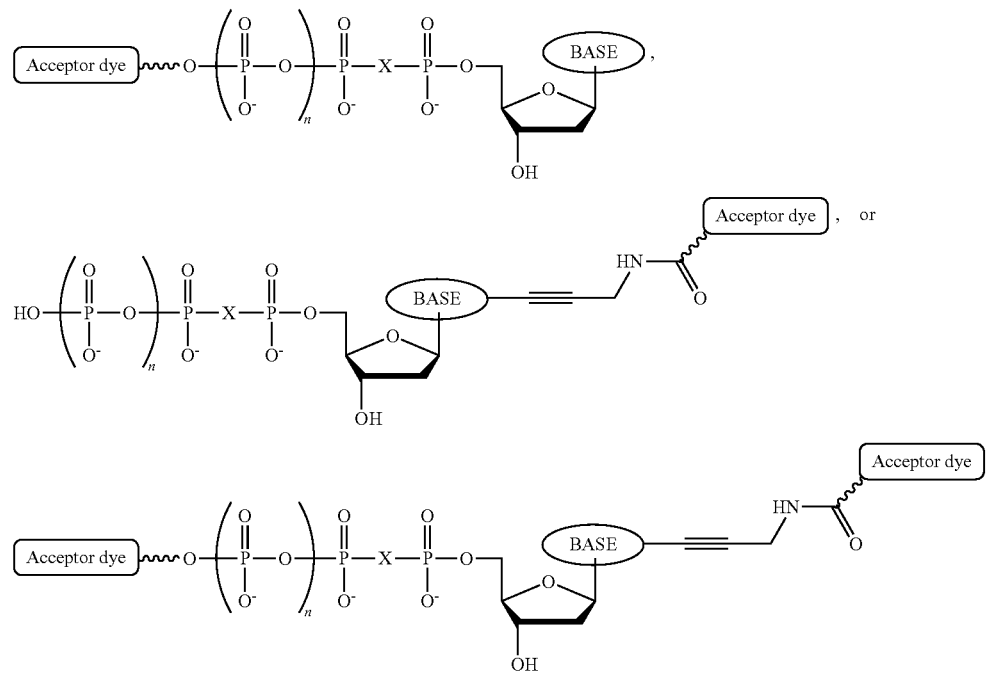

wherein the base is A, G, C, T, or U, or analogues thereof, wherein X is $CH_2$, NH, CHF, or $CF_2$, wherein n is 0, 1, 2, 3, or 4, wherein the acceptor dye is a fluorophore, and wherein X prevents a nucleotide polymerase from hydrolyzing the bond between the α and β phosphates wherein the nucleotide polymerase has attached, incorporated, and/or conjugated fluorescence donor molecules, wherein the donor molecules are Förster Resonance Energy Transfer (FRET) donors, and the acceptor dyes on the nucleotide analogue are corresponding FRET acceptors, under conditions permitting the DNA polymerase to form a ternary complex with the single-stranded DNA, primer, and nucleotide analogue if the analogue has a base that is complementary to a nucleotide residue of the single-stranded DNA which is immediately 5' to a nucleoside residue of the single-stranded DNA hybridized to the 3' terminal nucleotide residue of the primer, and if the base of the nucleotide analogue is not complementary to the nucleotide residue of the single-stranded DNA which is immediately 5' to the nucleoside residue of the single-stranded DNA hybridized to the 3' terminal nucleotide residue of the primer, iteratively repeating the contacting with a different nucleotide analogue until the analogue is complementary to the nucleotide residue of the single-stranded DNA which is immediately 5' to the nucleotide residue of the single-stranded DNA hybridized to the 3' terminal nucleotide residue of the primer, thus forming a ternary complex, with the proviso that (i) the type of base on each nucleotide analogue is different from the type of base on each of the other nucleotide analogues, and (ii) the fluorophore of each nucleotide analogue has a predetermined fluorescent wavelength emission;

b) excite the nucleotide polymerase donor fluorescent molecules using an appropriate spectral emission, thereby causing the corresponding FRET acceptors, which are the acceptor dye organic fluorophores attached to the nucleotide analogue in the ternary complex, to generate the predetermined fluorescent wavelength emission, and thereby determine the identity of the nucleotide analogue;

c) contact the ternary complex with 3'-O blocked nucleotide reversible terminators under conditions permitting the nucleotide polymerase to catalyze incorporation onto the primer of a 3'O-blocked nucleotide reversible terminator complementary to a nucleotide residue of the single-stranded DNA which is immediately 5' to a nucleotide residue of the single-stranded DNA hybridized to the 3' terminal nucleotide residue of the primer, thereby replacing the nucleotide analogue in the ternary complex, wherein the 3'-O blocked nucleotide reversible terminators have the structure:

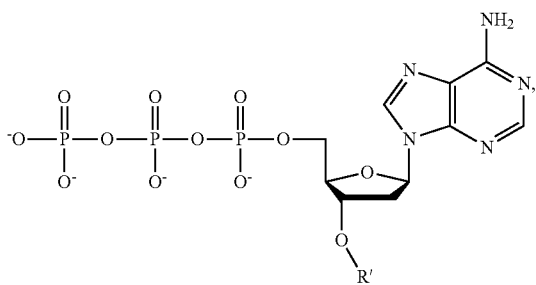

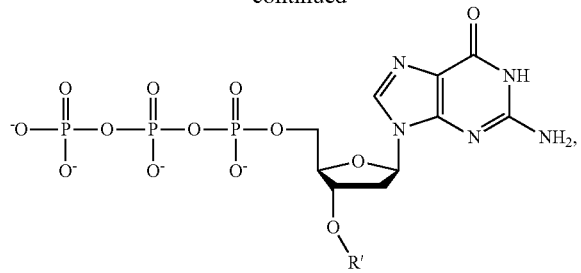

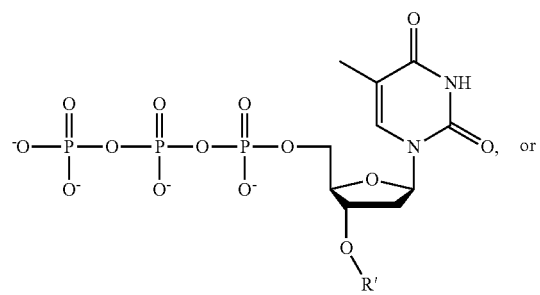

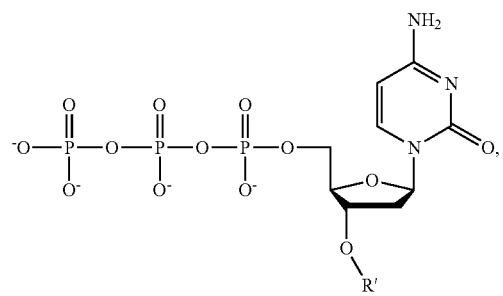

wherein R' is a cleavable linker bound to a blocking moiety, and wherein cleaving the linker results in a 3'-OH;

d) cleaving the linker bound to the blocking moiety of the incorporated 3'-O blocked nucleotide reversible terminator, thereby resulting in a 3'-OH;

e) iteratively performing steps a) through d) for each nucleotide residue of the single-stranded DNA to be sequenced so as to thereby determine the sequence of the single-stranded DNA.

This invention also provides a method for determining the nucleotide sequence of a single-stranded DNA comprising:

a) contacting a composition comprising a single-stranded DNA which has a primer hybridized to a portion thereof, a nucleotide polymerase, and four nucleotide analogues having the structure:

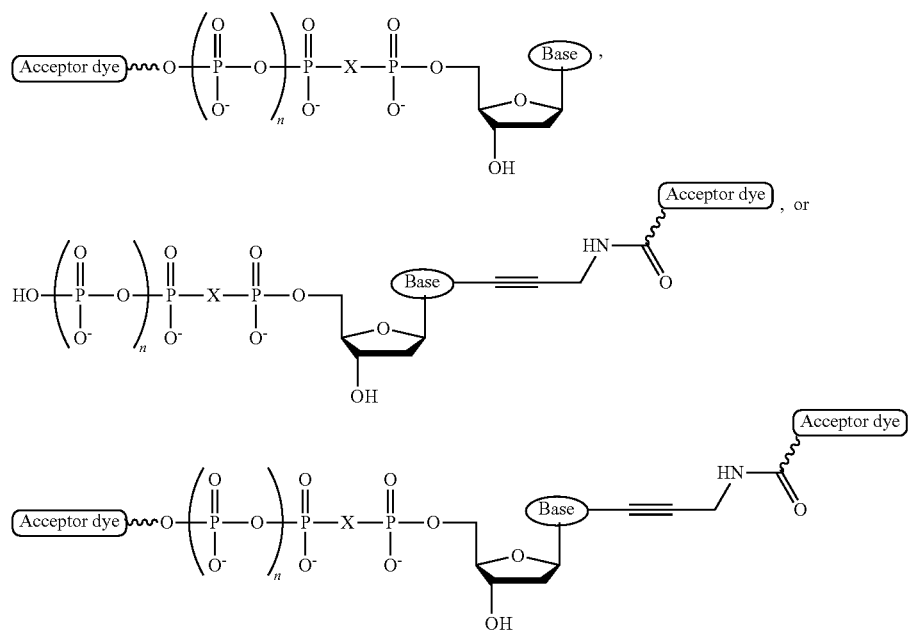

wherein the base is adenine, guanine, cytosine, uracil, thymine, or analogues thereof, wherein n is 0, 1, 2, 3, or 4, wherein the acceptor dye is one or more fluorophores, and wherein X prevents a nucleotide polymerase from hydrolyzing the bond between the α and β phosphates, wherein the nucleotide polymerase has attached, incorporated, and/or conjugated fluorescence donor molecules, wherein the donor molecules are Förster Resonance Energy Transfer (FRET) donors, and the acceptor dyes on the nucleotide analogue are corresponding FRET acceptors, wherein (i) the type of base on each analogue is different from the type of base on each of the other three analogues, (ii) the fluorophores of each nucleotide analogue have a unique predetermined fluorescent wavelength emission that corresponds to the type of base, and (iii) the fluorophores of each analogue are FRET acceptors that are excited by same donor fluorescence molecules in the nucleotide polymerase;

under conditions permitting the nucleotide polymerase to form a ternary complex with the single-stranded DNA, primer, and a nucleotide analogue wherein the nucleotide analogue has a base that is complementary to a nucleotide residue of the single-stranded DNA which is immediately 5' to a nucleoside residue of the single-stranded DNA hybridized to the 3' terminal nucleotide residue of the primer, b) exciting the nucleotide polymerase fluorescent donor molecules using an appropriate spectral emission, thereby causing the corresponding FRET acceptors, which are the acceptor dye fluorophores attached to the nucleotide analogue in the ternary complex, to generate the unique predetermined fluorescent wavelength emission, and thereby determine the identity of the nucleotide analogue;

c) contact the ternary complex with 3'-O blocked nucleotide reversible terminators under conditions permitting the nucleotide polymerase to catalyze incorporation onto the primer of a 3'O-blocked nucleotide reversible terminator complementary to a nucleotide residue of the single-stranded DNA which is immediately 5' to a nucleotide residue of the single-stranded DNA hybridized to the 3' terminal nucleotide residue of the primer, thereby replacing the nucleotide analogue in the ternary complex, wherein the 3'-O blocked nucleotide reversible terminators have the structure:

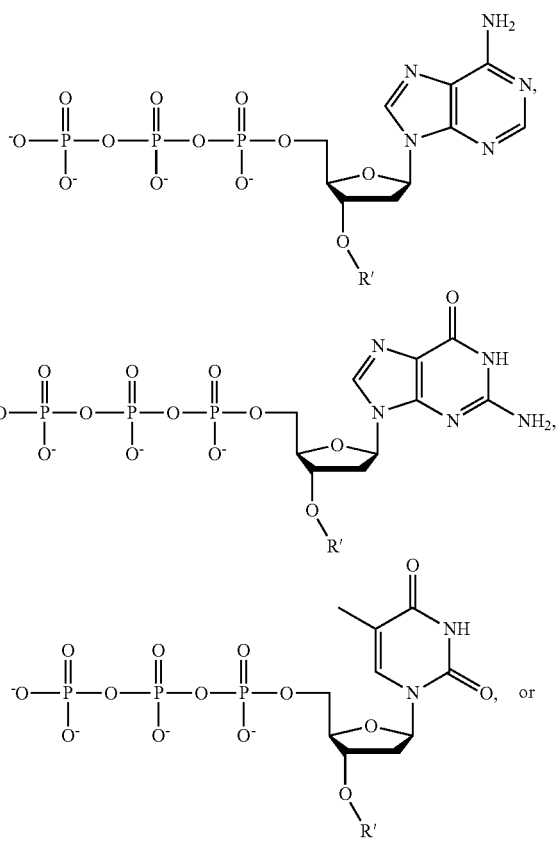

-continued

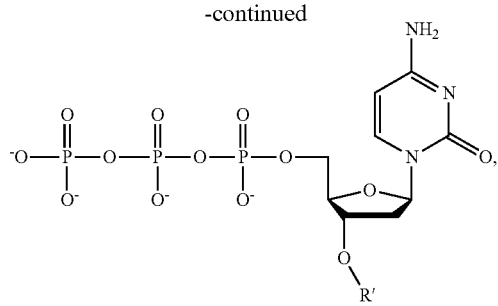

wherein R' is a cleavable linker bound to a blocking moiety, and wherein cleaving the linker results in a 3'-OH;
d) cleaving the linker bound to the blocking moiety of the incorporated 3'-O blocked nucleotide reversible terminator, thereby resulting in a 3'-OH;
e) iteratively performing steps a) through d) for each nucleotide residue of the single-stranded DNA to be sequenced so as to thereby determine the sequence of the single-stranded DNA.

This invention also provides a real-time method for determining the nucleotide sequence of a single-stranded DNA comprising:
a) contacting a composition comprising a single-stranded DNA which has a primer hybridized to a portion thereof, a nucleotide polymerase, and four nucleotide analogues having the structure:

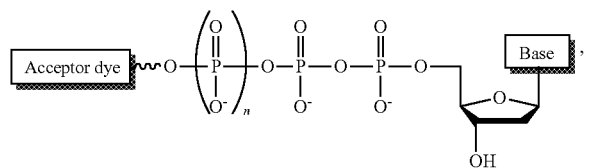

wherein the base is A, G, C, T, or U, or analogues thereof, wherein n is 0, 1, 2, 3, or 4, wherein the acceptor dye is one or more fluorophores,
under conditions permitting the nucleotide polymerase to incorporate a nucleotide analogue when the nucleotide analogue has a base that is complementary to a nucleotide residue of the single-stranded DNA which is immediately 5' to a nucleotide residue of the single-stranded DNA hybridized to the 3' terminal nucleotide residue of the primer, and wherein the nucleotide polymerase has attached or incorporated fluorescence donor molecules,
wherein the nucleotide polymerase has attached, incorporated, and/or conjugated fluorescence donor molecules, wherein the donor molecules are Förster Resonance Energy Transfer (FRET) donors, and the acceptor dyes and the acceptor dyes on the nucleotide analogue are corresponding FRET acceptors;
b) exciting the nucleotide polymerase fluorescence donor molecules using an appropriate spectral emission, thereby causing the corresponding FRET acceptors attached to the nucleotide analogues, to generate the unique predetermined fluorescent wavelength emission, and thereby determine the identity of the nucleotide analogue;
c) iteratively performing steps a) through b) for each nucleotide residue of the single-stranded DNA to be sequenced so as to thereby determine the sequence of the single-stranded DNA.

In a further embodiment the acceptor dye is 2, or 3 organic fluorophores. In a further embodiment the organic fluorophore is a cyanine dye, a rhodamine dye, fluorescein, acridine, coumarin, Texas Red dye, BODIPY, GFP, rhodol, ROX, resorfuin, Alexa Flour, quantum dot, Tokyo Green, N,N,N',N'-tetramethyl-6-carboxyrhodamine, or In a further embodiment the polymerase fluorescence donor molecules are one or more of a cyanine dye, a rhodamine dye, fluorescein, acridine, coumarin, Texas Red dye, BODIPY, GFP, rhodol, ROX, resorfuin, Alexa Flour, a quantum dot, Tokyo Green, an Ru(II) polypyridyl complex, N,N,N',N'-tetramethyl-6-carboxyrhodamine, or any derivative thereof.

In a further embodiment the cleavable linker is photocleavable or chemically cleavable.

In a further embodiment the cleavable linker is any one of an allyl group, alkyl group, carbonyl group, Sieber linkers, indole, disulfide, dithiomethyl, azidomethyl, nitrobenzyl group.

In a further embodiment the cleavable linker is cleaved using Pd(0), tetrabutylammonium, DTT, a triphosphine, peroxydisulphate, iodine, or any derivative thereof.

In a further embodiment optionally a buffer wash occurs after each of steps a), b), c), and/or d).

In a further embodiment the primer or single-stranded DNA are bound to a magnetic bead or the surface of a fluidic chamber.

In a further embodiment the polymerase the primer or single-stranded DNA are bound to the magnetic bead or surface are modified with one of amino, sulfhydryl, or biotin moieties.

In a further embodiment, the single-stranded DNA is amplified using emulsion PCR thereby resulting in a plurality of copies of the single-stranded DNA.

In a further embodiment the method is simultaneously performed on the plurality of single-stranded DNA copies.

In another embodiment prior to step a), several copies of the single-stranded DNA are created on a bead using emulsion PCT.

In another embodiment prior to step a), several copies of the single-stranded DNA are created on a surface using bridge amplification.

In another embodiment the single-stranded DNA is bound to a surface and remains there during the iterative process.

In another embodiment prior to step a) catalytic metal ions are removed.

In another embodiment the acceptor dye is 1, 2, or 3 organic fluorophores.

In another embodiment the organic fluorophores are separated by a separation distance that prevents the organic fluorophores from significantly quenching each other.

In an embodiment when the ternary complex is formed, the nucleotide polymerase fluorescence donor molecule and the nucleoside polyphosphate analogue acceptor fluorophore are less than 10 nm from each other.

In an embodiment the nucleotide polymerase fluorescence donor molecule and the nucleoside polyphosphate analogue acceptor fluorophore are between 2 nm-4 nm from each other.

In an embodiment time-gated luminescence detection techniques are used to detect the nucleoside polyphosphate analogue acceptor emission signal.

In an embodiment the nucleotide polymerase is a mutant *Geobacillus kaustophilus* DNA polymerase I or Phi29 DNA polymerase.

In an embodiment the polymerase has pairs of cysteines in antipodal locations wherein the fluorescence donor molecules are attached.

This invention also provides a method for determining the nucleotide sequence of a single-stranded DNA comprising:
a) contacting a composition comprising a single-stranded DNA, wherein the single-stranded DNA has a primer hybridized to a portion thereof, with a non-catalytic metal ion, a nucleotide polymerase, and a nucleotide analogue having the structure:

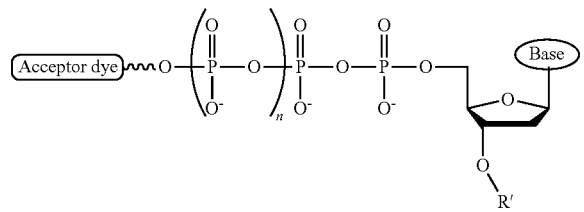

wherein the base is A, G, C, T, or U, or analogues thereof, wherein n is 0, 1, 2, 3, or 4, wherein the acceptor dye is one or more fluorophores, wherein R' is a cleavable linker bound to a blocking moiety, and wherein cleaving the linker results in a 3'-OH,
wherein the nucleotide polymerase has attached, incorporated, and/or conjugated fluorescence donor molecules, wherein the donor molecules are Förster Resonance Energy Transfer (FRET) donors, and the acceptor dyes on the nucleotide analogue are corresponding FRET acceptors,
wherein (i) the type of base on each analogue is different from the type of base on each of the other three analogues, (ii) the fluorophores of each nucleotide analogue have a unique predetermined fluorescent wavelength emission that corresponds to the type of base, and (iii) the fluorophores of each analogue are FRET acceptors that are excited by same donor fluorescence molecules in the nucleotide polymerase;
under conditions permitting the nucleotide polymerase to form a ternary complex with the single-stranded DNA, primer, and a nucleotide analogue wherein the nucleotide analogue has a base that is complementary to a nucleotide residue of the single-stranded DNA which is immediately 5' to a nucleoside residue of the single-stranded DNA hybridized to the 3' terminal nucleotide residue of the primer;
b) exciting the nucleotide polymerase fluorescence donor molecules using an appropriate spectral emission, thereby causing the corresponding FRET acceptors, which are the acceptor dye fluorophores attached to the nucleotide analogue in the ternary complex, to generate the unique predetermined fluorescent wavelength emission, and thereby determine the identity of the nucleotide analogue;
c) contacting the ternary complex with catalytic metal ions permitting the nucleotide polymerase to incorporate the nucleotide analogue into the primer;
d) cleaving the linker bound to the blocking moiety of the incorporated analogue thereby resulting in a 3'-OH;
e) iteratively performing steps a) through d) for each nucleotide residue of the single-stranded DNA to be sequenced so as to thereby determine the sequence of the single-stranded DNA.

This invention also provides a method for determining the nucleotide sequence of a single-stranded DNA comprising:
a) contacting a composition comprising a single-stranded DNA, wherein the single-stranded DNA has a primer hybridized to a portion thereof, with a non-catalytic metal ion, a nucleotide polymerase, and four nucleotide analogues having the structure:

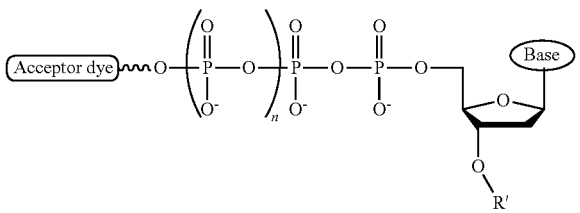

wherein the base is A, G, C, T, or U, or analogues thereof, wherein n is 0, 1, 2, 3, or 4, wherein the acceptor dye is one or more fluorophores, wherein R' is a cleavable linker bound to a blocking moiety, and wherein cleaving the linker results in a 3'-OH,
wherein the nucleotide polymerase has attached, incorporated, and/or conjugated fluorescence donor molecules, wherein the donor molecules are Förster Resonance Energy Transfer (FRET) donors, and the acceptor dyes on the nucleotide analogue are corresponding FRET acceptors,
under conditions permitting the nucleotide polymerase to form a ternary complex with the single-stranded DNA, primer, and a nucleotide analogue wherein the nucleotide analogue has a base that is complementary to a nucleotide residue of the single-stranded DNA which is immediately 5' to a nucleoside residue of the single-stranded DNA hybridized to the 3' terminal nucleotide residue of the primer,
b) exciting the nucleotide polymerase fluorescence donor molecules using an appropriate spectral emission, thereby causing the corresponding FRET acceptors, which are the acceptor dye fluorophores attached to the nucleotide analogue in the ternary complex, to generate the unique predetermined fluorescent wavelength emission, and thereby determine the identity of the nucleotide analogue;
c) contacting the ternary complex with catalytic metal ions permitting the nucleotide polymerase to incorporate the nucleotide analogue into the primer;
d) cleaving the linker bound to the blocking moiety of the incorporated analogue thereby resulting in a 3'-OH;
e) iteratively performing steps a) through d) for each nucleotide residue of the single-stranded DNA to be sequenced so as to thereby determine the sequence of the single-stranded DNA.

In a further embodiment the acceptor dye is 2, or 3 organic fluorophores. In a further embodiment the organic fluorophore is a cyanine dye, a rhodamine dye, fluorescein, acridine, coumarin, Texas Red dye, BODIPY, GFP, rhodol, ROX, resorfuin, Alexa Flour, quantum dot, Tokyo Green, N,N,N',N'-tetramethyl-6-carboxyrhodamine, or In a further embodiment the polymerase fluorescence donor molecules are one or more of a cyanine dye, a rhodamine dye, fluorescein, acridine, coumarin, Texas Red dye, BODIPY, GFP, rhodol, ROX, resorfuin, Alexa Flour, a quantum dot, Tokyo Green, an Ru(II) polypyridyl complex, N,N,N',N'-tetramethyl-6-carboxyrhodamine, or any derivative thereof.

In a further embodiment the cleavable linker is photocleavable or chemically cleavable.

In a further embodiment the cleavable linker is any one of an allyl group, alkyl group, carbonyl group, Sieber linkers, indole, disulfide, dithiomethyl, azidomethyl, nitrobenzyl group.

In a further embodiment the cleavable linker is cleaved using Pd(0), tetrabutylammonium, DTT, a triphosphine, peroxydisulphate, iodine, or any derivative thereof.

In a further embodiment optionally a buffer wash occurs after each of steps a), b), c), and/or d).

In a further embodiment the primer or single-stranded DNA are bound to a magnetic bead or the surface of a fluidic chamber.

In a further embodiment the polymerase the primer or single-stranded DNA are bound to the magnetic bead or surface are modified with one of amino, sulfhydryl, or biotin moieties.

In a further embodiment, the single-stranded DNA is amplified using emulsion PCR thereby resulting in a plurality of copies of the single-stranded DNA.

In a further embodiment the method is simultaneously performed on the plurality of single-stranded DNA copies.

In another embodiment prior to step a), several copies of the single-stranded DNA are created on a bead using emulsion PCT.

In another embodiment prior to step a), several copies of the single-stranded DNA are created on a surface using bridge amplification.

In another embodiment the single-stranded DNA is bound to a surface and remains there during the iterative process.

In another embodiment prior to step a) catalytic metal ions are removed.

In another embodiment the acceptor dye is 1, 2, or 3 organic fluorophores.

In another embodiment the organic fluorophores are separated by a separation distance that prevents the organic fluorophores from significantly quenching each other.

In an embodiment when the ternary complex is formed, the nucleotide polymerase fluorescence donor molecule and the nucleoside polyphosphate analogue acceptor fluorophore are less than 10 nm from each other.

In an embodiment the nucleotide polymerase fluorescence donor molecule and the nucleoside polyphosphate analogue acceptor fluorophore are between 2 nm-4 nm from each other.

In an embodiment time-gated luminescence detection techniques are used to detect the nucleoside polyphosphate analogue acceptor emission signal.

In an embodiment the nucleotide polymerase is a mutant *Geobacillus kaustophilus* DNA polymerase I or Phi29 DNA polymerase.

In an embodiment the polymerase has pairs of cysteines in antipodal locations wherein the fluorescence donor molecules are attached.

In an embodiment the non-catalytic metal ions are $Ca^{++}$ and/or $Sr++$.

In an embodiment the catalytic metal ions are $Mg^{++}$ and/or $M^{++}$.

For the foregoing embodiments, each embodiment disclosed herein is contemplated as being applicable to each of the other disclosed embodiments. In addition, the elements recited in the nucleotide analogue embodiments can be used in the composition and method embodiments described herein and vice versa.

As used herein, and unless stated otherwise, each of the following terms shall have the definition set forth below.
  A—Adenine;
  C—Cytosine;
  G—Guanine;
  T—Thymine;
  U—Uracil;
  DNA—Deoxyribonucleic acid;
  RNA—Ribonucleic acid;
  "Nucleic acid" shall mean, unless otherwise specified, any nucleic acid molecule, including, without limitation, DNA, RNA and hybrids thereof. In an embodiment the nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Substrate" or "Surface" shall mean any suitable medium present in the solid phase to which a nucleic acid or an agent may be affixed. Non-limiting examples include chips, beads, nanopore structures and columns. In an embodiment the solid substrate can be present in a solution, including an aqueous solution, a gel, or a fluid.

"Hybridize" shall mean the annealing of one single-stranded nucleic acid to another nucleic acid based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York). As used herein, hybridization of a primer sequence, or of a DNA extension product, to another nucleic acid shall mean annealing sufficient such that the primer, or DNA extension product, respectively, is extendable by creation of a phosphodiester bond with an available nucleotide or nucleotide analog capable of forming a phosphodiester bond.

As used herein, unless otherwise specified, a base which is "different from" another base or a recited list of bases shall mean that the base has a different structure from the other base or bases. For example, a base that is "different from" adenine, thymine, and cytosine would include a base that is guanine or a base that is uracil.

As used herein, unless otherwise specified, a tag moiety which is different from the tag moiety of a referenced molecule means that the tag moiety has a different chemical structure from the chemical structure of the other/referenced tag moiety.

In certain embodiments the underlying photophysical principle for this SBS method is based on Förster resonance energy transfer (FRET), where the energy of electronic excited states of a donor molecule is transferred to an acceptor molecule via non-radiative dipole-dipole interactions. As a result, the luminescence of the donor molecule is quenched and fluorescence of the acceptor molecule is observed. The occurrence and efficiency of FRET depends on various parameters, such as the distance (<10 nm) between the donor and acceptor as well as the spectral overlap between the donor luminescence and acceptor absorption spectra (Hung et al 1996, Turro et al 2010

In certain embodiments, the polymerase, single-stranded polynucleotide, RNA, or primer is bound to a solid substrate via 1,3-dipolar azide-alkyne cycloaddition chemistry. In an embodiment the polymerase, DNA, RNA, or primer, is bound to the solid substrate via a polyethylene glycol molecule. In an embodiment the polymerase, DNA, RNA, primer, or probe is alkyne-labeled. In an embodiment the polymerase, DNA, RNA, primer, or probe is bound to the solid substrate via a polyethylene glycol molecule and the solid substrate is azide-functionalized. In an embodiment the polymerase, DNA, RNA, or primer, is immobilized on the solid substrate via an azido linkage, an alkynyl linkage, or biotin-streptavidin interaction. Immobilization of nucleic acids is described in Immobilization of DNA on Chips II, edited by Christine Wittmann (2005), Springer Verlag, Berlin, which is hereby incorporated by reference. In an embodiment the DNA is single-stranded polynucleotide. In an embodiment the RNA is single-stranded RNA.

In other embodiments, the solid substrate is in the form of a chip, a bead, a well, a capillary tube, a slide, a wafer, a filter, a fiber, a porous media, a porous nanotube, or a column. This invention also provides the instant method, wherein the solid substrate is a metal, gold, silver, quartz, silica, a plastic, polypropylene, a glass, or diamond. This invention also provides the instant method, wherein the solid substrate is a porous non-metal substance to which is attached or impregnated a metal or combination of metals. The solid surface may be in different forms including the non-limiting examples of a chip, a bead, a tube, a matrix, a nanotube. The solid surface may be made from materials common for DNA microarrays, including the non-limiting examples of glass or nylon. The solid surface, for example beads/micro-beads, may be in turn immobilized to another solid surface such as a chip.

In various embodiments the polymerase, nucleic acid samples, DNA, RNA, primer, or probe are separated in discrete compartments, wells or depressions on a surface.

In this invention methods are provided wherein about 1000 or fewer copies of the polymerase, nucleic acid sample, DNA, RNA, or primer are bound to the substrate. This invention also provides the instant methods wherein $2\times10^7$, $1\times10^7$, $1\times10^6$ or $1\times10^4$ or fewer copies of the polymerase, nucleic acid sample, DNA, RNA, or primer are bound to the substrate or surface.

In some embodiments, the immobilized polymerase, nucleic acid sample, DNA, RNA, or primer, is immobilized at a high density. This invention also provides the instant methods wherein over or up to $1\times10^7$, $1\times10^8$, $1\times10^9$ copies of the polymerase, nucleic acid sample, DNA, RNA, or primer are bound to the substrate or surface.

In other embodiments of the methods and/or compositions of this invention, the DNA is single-stranded. In other embodiments of the methods or of the compositions described herein, the single-stranded polynucleotide is replaced with an RNA that is single-stranded.

In certain embodiments, UV light is used to photochemically cleave the photochemically cleavable linkers and moieties. In an embodiment, the photocleavable linker is a 2-nitrobenzyl moiety.

A "nucleotide residue" is a single nucleotide in the state it exists after being incorporated into, and thereby becoming a monomer of, a polynucleotide. Thus, a nucleotide residue is a nucleotide monomer of a polynucleotide, e.g. DNA, which is bound to an adjacent nucleotide monomer of the polynucleotide through a phosphodiester bond at the 3' position of its sugar and is bound to a second adjacent nucleotide monomer through its phosphate group, with the exceptions that (i) a 3' terminal nucleotide residue is only bound to one adjacent nucleotide monomer of the polynucleotide by a phosphodiester bond from its phosphate group, and (ii) a 5' terminal nucleotide residue is only bound to one adjacent nucleotide monomer of the polynucleotide by a phosphodiester bond from the 3' position of its sugar.

Because of well-understood base-pairing rules, determining the FRET energy electronic excited states of the nucleoside polyphosphate analogue incorporated into a primer or DNA extension product, and thereby the identity of the dNTP analog that was incorporated, permits identification of the complementary nucleotide residue in the single-stranded polynucleotide that the primer or DNA extension product is hybridized to. Thus, if the dNTP analog that was incorporated has a unique wavenumber in the Raman spectroscopy peak identifying it as comprising an adenine, a thymine, a cytosine, or a guanine, then the complementary nucleotide residue in the single-stranded polynucleotide is identified as a thymine, an adenine, a guanine or a cytosine, respectively. The purine adenine (A) pairs with the pyrimidine thymine (T). The pyrimidine cytosine (C) pairs with the purine guanine (G). Similarly, with regard to RNA, if the dNTP analog that was incorporated comprises an adenine, a uracil, a cytosine, or a guanine, then the complementary nucleotide residue in the single-stranded RNA is identified as a uracil, an adenine, a guanine or a cytosine, respectively.

Incorporation into an oligonucleotide or polynucleotide (such as a primer or DNA extension strand) of a nucleotide and/or nucleoside analog means the formation of a phosphodiester bond between the 3' carbon atom of the 3' terminal nucleotide residue of the polynucleotide and the 5' carbon atom of the dNTP analog resulting in the loss of pyrophosphate from the dNTP analog.

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention.

As used herein, "alkyl" includes both branched and straight-chain saturated aliphatic hydrocarbon groups having the specified number of carbon atoms and may be unsubstituted or substituted. Thus, C1-Cn as in "C1-Cn alkyl" includes groups having 1, 2, . . . , n-1 or n carbons in a linear or branched arrangement. For example, a "C1-C5 alkyl" includes groups having 1, 2, 3, 4, or 5 carbons in a linear or branched arrangement, and specifically includes methyl, ethyl, n-propyl, isopropyl, n-butyl, t-butyl, and pentyl.

As used herein, "alkenyl" refers to a non-aromatic hydrocarbon group, straight or branched, containing at least 1 carbon to carbon double bond, and up to the maximum possible number of non-aromatic carbon-carbon double bonds may be present, and may be unsubstituted or substituted. For example, "C2-C5 alkenyl" means an alkenyl group having 2, 3, 4, or 5, carbon atoms, and up to 1, 2, 3, or 4, carbon-carbon double bonds respectively. Alkenyl groups include ethenyl, propenyl, and butenyl.

The term "alkynyl" refers to a hydrocarbon group straight or branched, containing at least 1 carbon to carbon triple bond, and up to the maximum possible number of non-aromatic carbon-carbon triple bonds may be present, and may be unsubstituted or substituted. Thus, "C2-C5 alkynyl" means an alkynyl group having 2 or 3 carbon atoms and 1 carbon-carbon triple bond, or having 4 or 5 carbon atoms and up to 2 carbon-carbon triple bonds. Alkynyl groups include ethynyl, propynyl and butynyl.

The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable nucleotide analogue. Substituted groups also include groups in which one or more bonds to a carbon(s) or hydrogen(s) atom are replaced by one or more bonds, including double or triple bonds, to a heteroatom. Non-limiting examples of substituents include the functional groups described above, and for example, N, e.g. so as to form —CN.

It is understood that substituents and substitution patterns on the nucleotide analogues of the instant invention can be selected by one of ordinary skill in the art to provide nucleotide analogues that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the nucleotide analogues of the present invention, one of ordinary skill in the art will recognize that the various substituents, i.e. $R_1$, $R_2$, etc. are to be chosen in conformity with well-known principles of chemical structure connectivity.

In the nucleotide analogue structures depicted herein, hydrogen atoms, except on ribose and deoxyribose sugars, are generally not shown. However, it is understood that sufficient hydrogen atoms exist on the represented carbon atoms to satisfy the octet rule.

All combinations of the various elements described herein are within the scope of the invention. All sub-combinations of the various elements described herein are also within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Disclosed herein is a FRET based sequencing by synthesis (SBS) approach, in which a polymerase molecule is conjugated to 1 or more fluorescence donor molecules (fluorophores at a higher energy/lower wavelength than a particular acceptor fluorophore). The positions selected for attachment have the following properties: (1) they do not interfere with the polymerase enzymatic function, i.e., they should be excluded from the key binding pockets and active center of the enzyme as well as other amino acids required for enzyme activity; and (2) they are distributed over the enzyme surface so as to produce a localized FRET between the donor fluorophores on the polymerase and the acceptor fluorophores on the incoming nucleotide. FRET typically acts at a distance in the range of 1-10 nm. Given that most polymerases have dimensions in the 4-10 nm range, placement of 1-3 donor molecules should accomplish this objective, allowing the donor to be localized within 3 nm of the acceptor-labeled nucleotide. Disclosed herein is substantial information obtained by generating mutants of several DNA polymerases that do not inhibit enzyme activity that are used to further refine these positions. As an example, *Geobacillus kaustophilus* DNA polymerase I mutants were produced with pairs of cysteines in various antipodal locations that could be used for attachment of energy donor molecules (FIG. 1) such as quantum dots (Nikiforov et al 2010, Peng et al 2012), organic fluorophors, or Ru(II) polypyridyl complexes (Marti et al 2007). Many additional positions for attachment of the donor dyes in this polymerase, and by extension other polymerases, to meet these requirements. Best positions for placement vary with the intensity of the donor emission and the size of the donor molecules. Moreover, the wavelengths for donor emission and acceptor absorbance have to be carefully selected to maximize FRET while minimizing competitive absorption. It has been demonstrated that particles as large as quantum dots can be attached to Phi29 DNA polymerase (Nikiforov et al 2010); these could be useful because their photophysical properties can be varied over a wide range. Quantum dots with light absorption over a broad wavelength range, but with narrow bandpass and high extinction coefficients, are available to optimize the donor absorption properties with the excitation light source. Luminescence lifetimes in quantum dots are often longer than most organic fluorophores, which increases the probability of FRET to the acceptor. Further increase of the donor luminescence lifetime is possible with the use of metal complexes, such as Ru(II) polypyridyl complexes as donors. Because energy transfer from the long-lived metal to ligand charge transfer (MLCT) excited state to singlet states of organic fluorophores, such as Cy5, is spin-forbidden, this energy transfer is slow, which results in a delayed fluorescence of the acceptor fluorophore (Marti et al 2007). Using time-gated luminescence detection techniques, such as fluorescence lifetime microscopy, the background signal originating from light scattering, autofluorescence, and direct excitation of the acceptor fluorophores can be eliminated.

Figure 2:
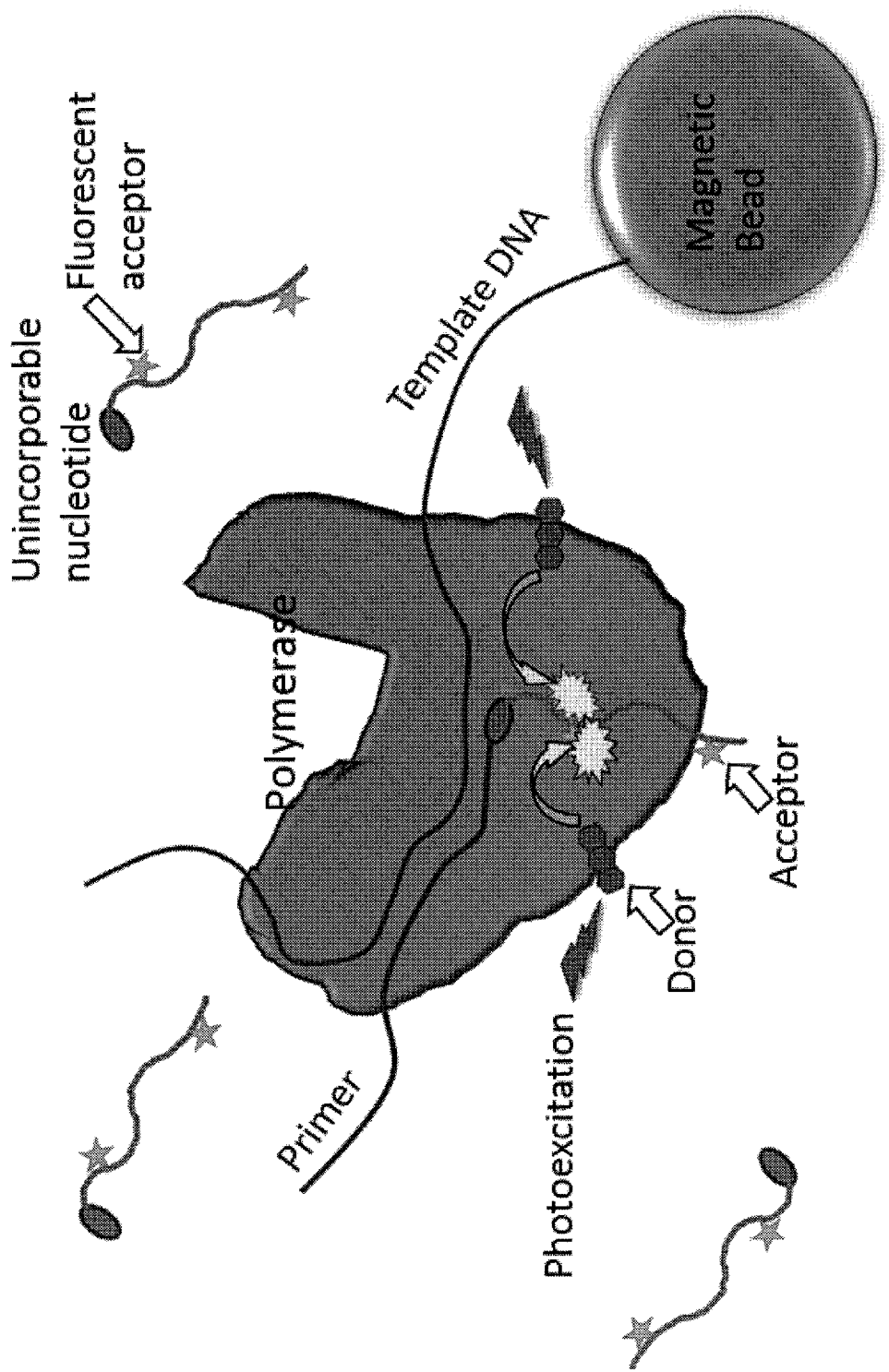
FIG. 2: FRET-based SBS with donor dyes bound to polymerase, acceptor dyes bound to nucleotide, and template attached to magnetic beads. Reaction is carried out in solution in microscopic chambers. The donor dye(s) is attached to the polymerase. Acceptor dyes are bound to the base and/or terminal phosphate of natural or reversibly blocked nucleotides. The arrows in the figure indicate excitation of the donor, FRET between donor and acceptor, and acceptor emission. With primer or template molecules bound to magnetic beads to restrict localization of the resulting complex and permit washing, sequencing reactions can be carried out in both single molecule or ensemble mode (see Examples 1 and 2 in text for details). DNA can also be attached directly to the chamber surface.
Figure 3:
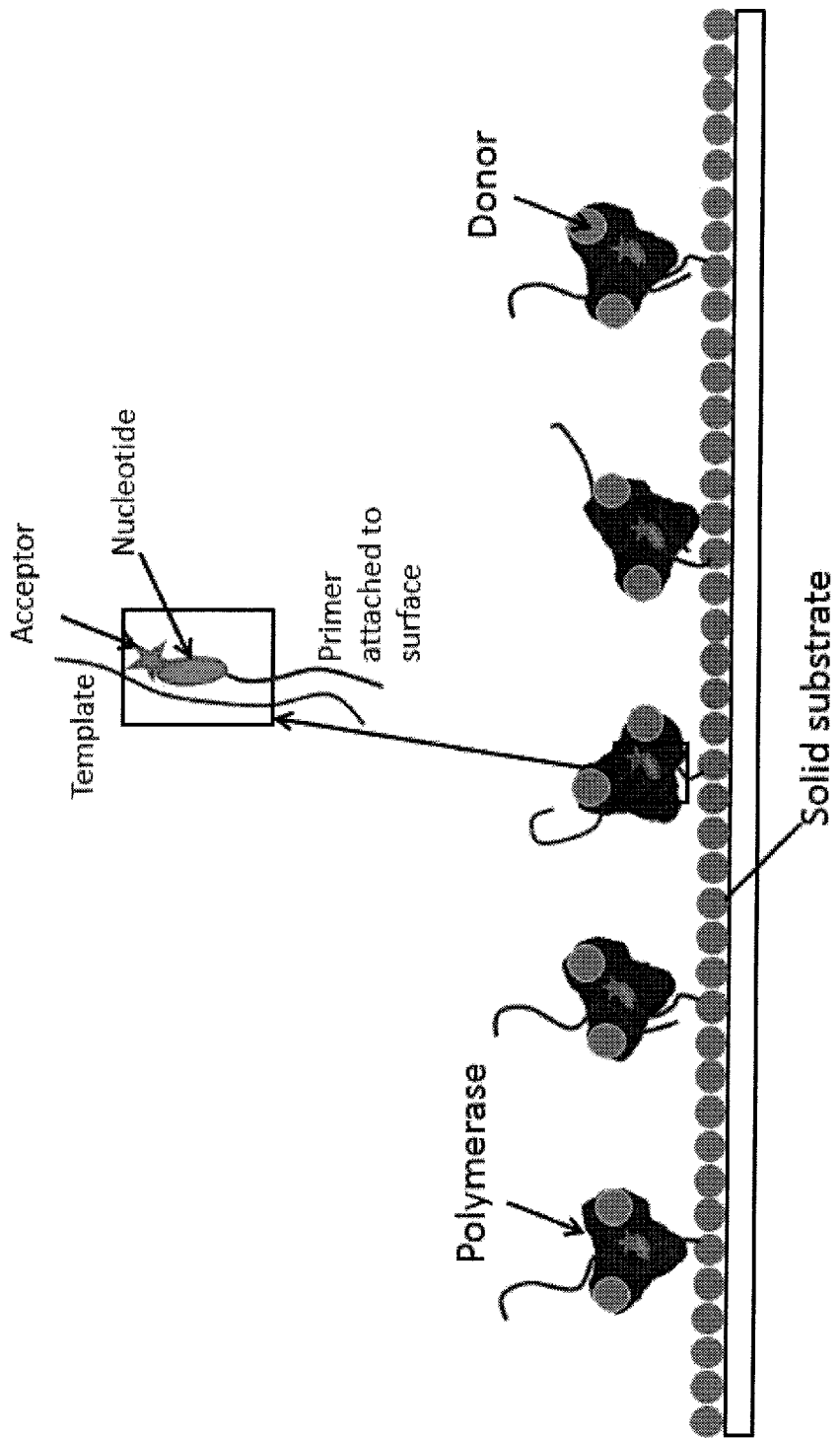
FIG. 3: Set-up similar to FIG. 2 except that primer is attached to magnetic beads or chamber surface. This permits single-molecule sequencing.

Two different setups for carrying out SBS using intermolecular FRET are depicted in FIGS. 2 and 3. In the first, the DNA is linked to magnetic beads or the surface of the fluidic chamber. Either the template (shown) or the primer may be attached to the surface. Many different linkage strategies are available. For instance the DNA may be modified with amino, sulfhydryl, or biotin moieties and reacted with beads derivatized with NHS succinimide, maleimide and streptavidin, respectively. Other chemical pairs, including but not limited to azide-alkyne and trans-cyclooctene-tetrazine, are also feasible. Many homobifunctional and heterobifunctional cross-linkers of assorted lengths are commercially available, including photoactivatable ones. If instead, adaptors are attached to the beads, it is possible to amplify the DNA by emulsion PCR to allow ensemble sequencing. In this case, an excess of polymerase in solution will interact with many of the templates on the same bead. In the second setup, the donor dye-decorated polymerases will be directly conjugated to the magnetic beads or solid surface. Again, many linkage strategies are available in addition to the biotin-Streptavidin pair shown in FIG. 3.

Since the efficiency of energy transfer is inversely proportional to the sixth power of the distance between donor and acceptor, it is unlikely that free nucleotides in solution will participate in energy transfer and so not contribute to the acceptor emission. Though not the preferred format, the acceptor dyes can be attached to the polymerase and a donor dye to the nucleotide, and would be limited to single color sequencing.

SBS can be performed in one-color mode with the same acceptor fluorophore on each of the four nucleotides. In this case, these nucleotides are added sequentially one by one in the course of the sequencing reaction. A four-color sequencing mode is possible with the use of multiple donor and/or acceptor dyes in conjunction with combinatorial energy transfer to generate unique fluorescence signatures for each of the four nucleotides. Previously, we have demonstrated that with one type of donor dye (e.g. fluorescein) and two acceptor fluorophores (e.g. N,N,N',N'-tetramethyl-6-carboxyrhodamine and cyanine-5) several distinct fluorescence signatures can be generated by varying the distance between the fluorophores (Ju et al 1995, Hung et al 1996, Tong et al 2001).

Figure 4:
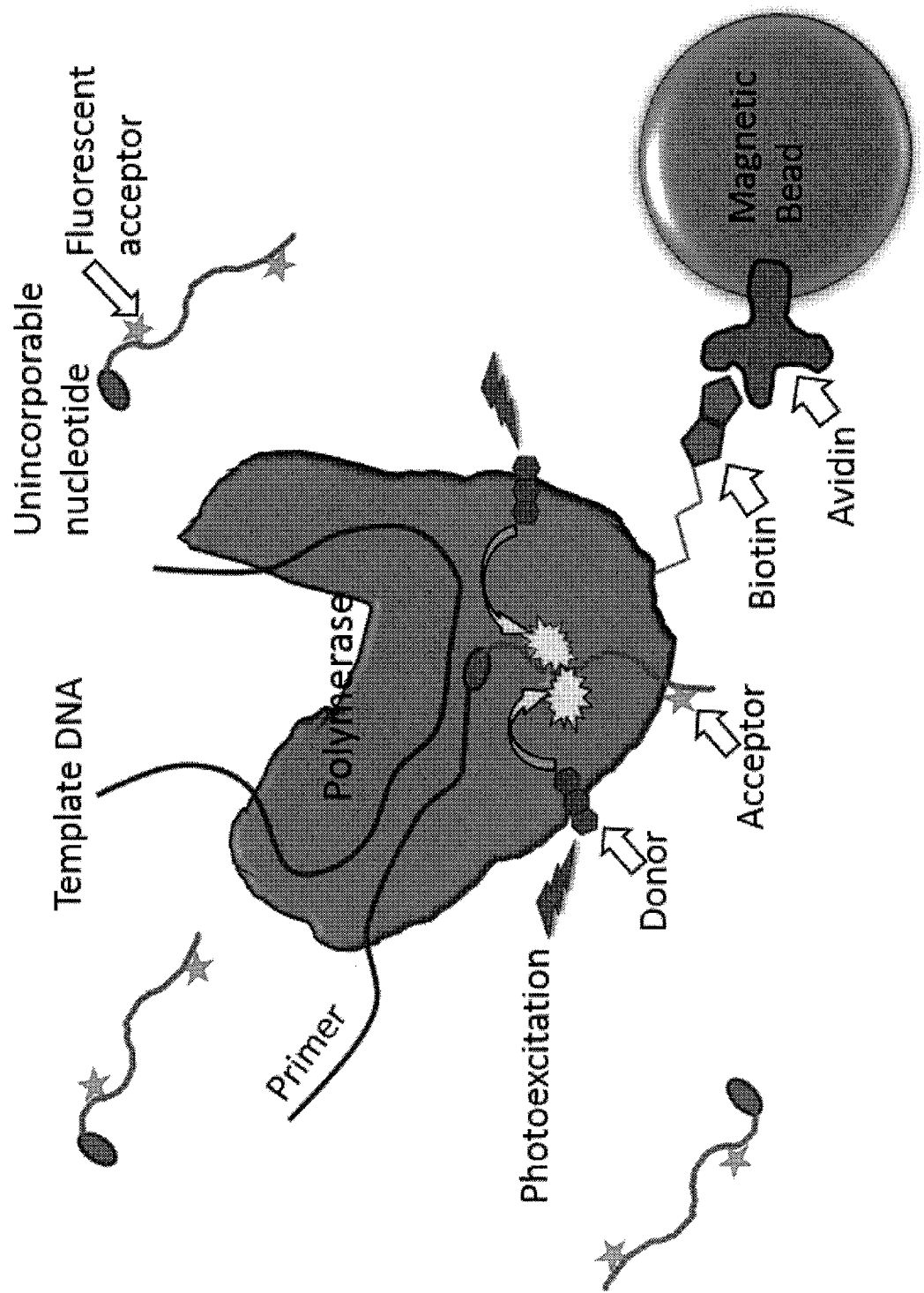
FIG. 4: FRET-based SBS with donor dyes bound to polymerase, acceptor dyes bound to nucleotide, and polymerase bound to magnetic beads. The biotin on the polymerase permits attachment to streptavidin beads allowing washing. Nucleotides in solution are beyond the Förster resonance distance that will give a detectable acceptor emission signal. The arrows in the figure indicate excitation of the donor, FRET between donor and acceptor, and acceptor emission. This set-up is designed for single molecule real time sequencing provided each of the four nucleotides has a different acceptor dye or FRET pair. DNA can also be attached directly to the chamber surface.

Herein disclosed are three experimental examples of sequencing approaches. Experiments 1-2 utilize the setup shown in FIG. 2, while Experiment 3 uses the setup shown in FIG. 3 (template attached to surface for single molecule or ensemble sequencing) or FIG. 4 (primer attached to surface for single molecule sequencing). For single molecule methods, random template libraries are allowed to attach to the beads or fluidic chamber surface individually. Alternatively, for ensemble sequencing, individual DNA molecules may be amplified on the magnetic beads by emulsion PCR or on the surface of the chamber by bridge amplification. Experiment 3 is a real-time single molecule sequencing approach.

Experiment 1: FRET-based SBS with donor dye on polymerase, acceptor dye on terminal phosphate and base of unincorporable nucleotides.

Figure 5:
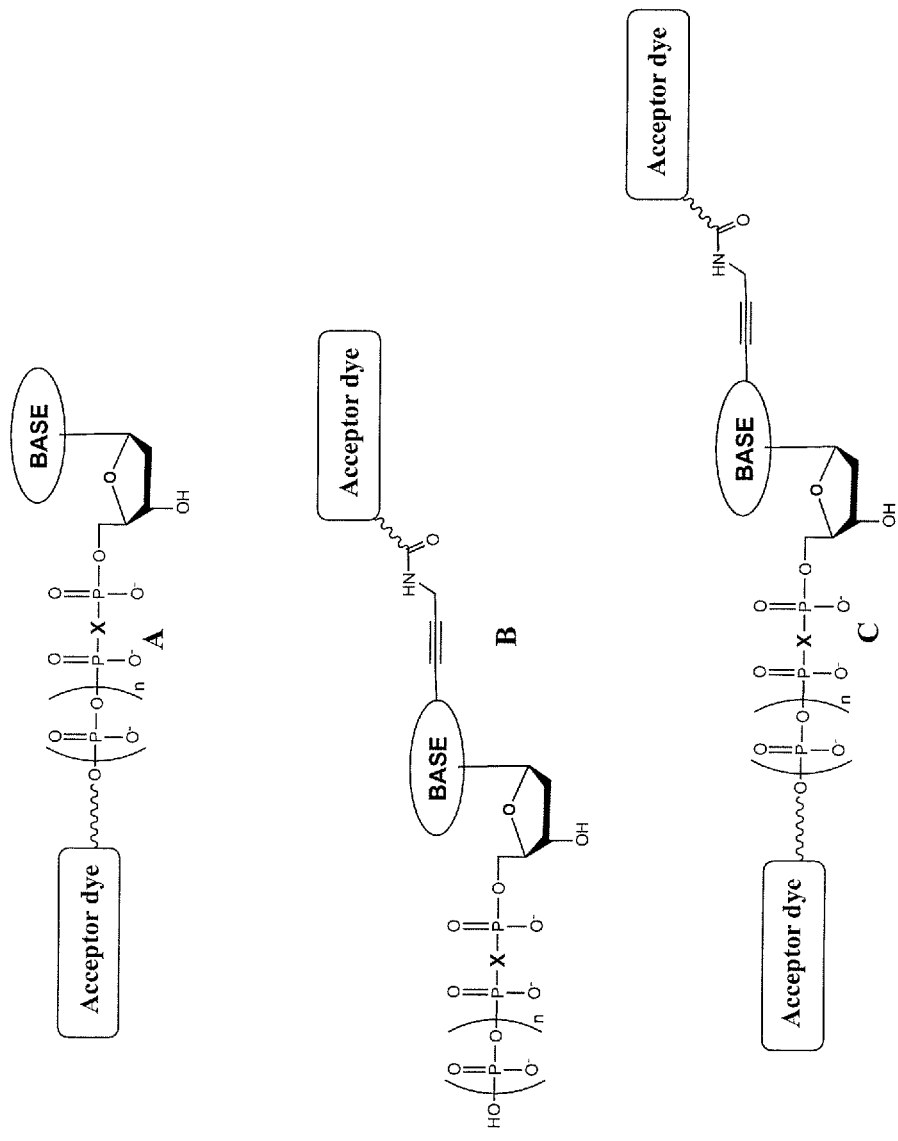
FIG. 5: Examples of fluorescent labeled non-incorporable nucleotides. Acceptor fluorophores can be attached at terminal phosphate (A), base (B) and or to both terminal phosphate and base (C).
Figure 6:
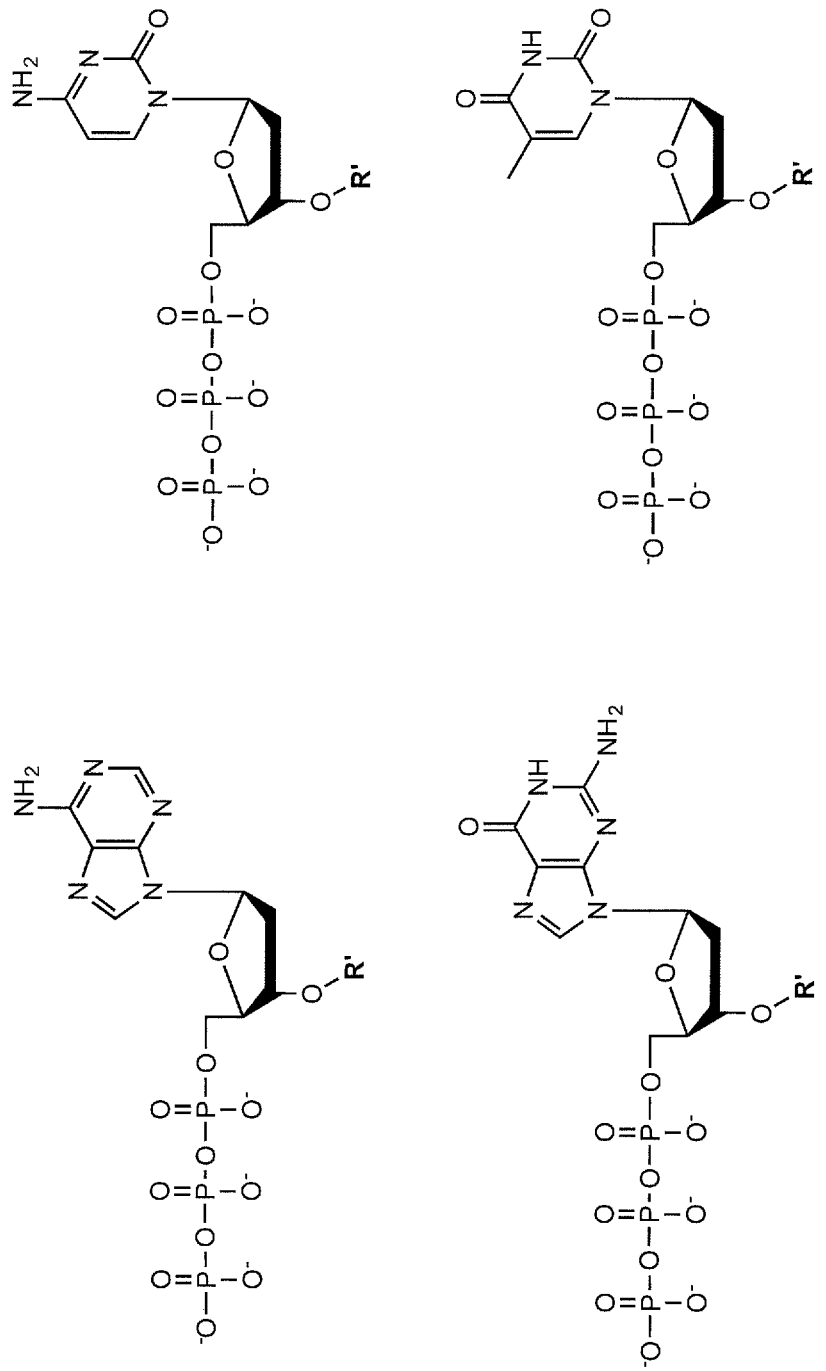
FIG. 6: Examples of 3'-O-reversibly blocked dNTPs for fluorescent sequencing.

This SBS reaction uses un-incorporable nucleotides, $\alpha$, $\beta$-X-2'-deoxynucleoside 5'-triphosphates (PCP-dNTPs) or polyphosphates (PCP-dNPPs), where X can be $CH_2$, NH, CHF or $CF_2$ (Upton et al 2009) and where the terminal phosphate and/or the base is derivatized with one to three acceptor fluorophores, where the separation distance between is tuned to avoid self-quenching (FIG. 5). These are added to the reaction chamber containing the bead-bound template (primer), free primer (template), and donor-decorated polymerase, resulting in the formation of a ternary complex consisting of polymerase, template, primer and nucleotide. A magnet placed below the reaction chamber will attract the beads with the bound ternary complexes to the bottoms of the chambers. This allows for multiple solution changes, and ensures precise localization over many cycles of sequencing. Because cleavage of the $\alpha$, $\beta$ bond in these nucleotides cannot take place, they are unable to be incorporated into DNA. Thus the ternary complex is monitored for sufficient time to obtain a convincing FRET signal using a TIRF or other appropriate fluorescent detection device. Excitation of the donor dye at an appropriate wavelength induces energy transfer from the donor to the acceptor fluorophores, generating a unique emission signal for the acceptor dye. Donor-acceptor dye pairs (e.g., high absorption cross-section cyanine dye as donor with Cy5 as acceptor, quantum dot donor with ROX acceptor) are selected with some spectral overlap but where competitive absorption is minimized. The chamber is then flushed with a high concentration of unlabeled NRTs. These replace the non-hydrolyzable phosphate nucleotide in the ternary complex and be incorporated. The NRTs may have any of a variety of blocking groups attached to the 3'-OH as shown in FIG. 6 such as allyl or azidomethyl groups (Guo et al 2008, Ju et al 2006). Following the addition of the appropriate chemical (Pd(0) or tetrabutylammonium peroxydisulphate/iodine for allyl, LiBF4 for methoxymethyl (Lipschutz et al 1982, Ireland and Varney 1986), TCEP for azidomethyl and disulfide) or light (in the case of the 2-nitrobenzyl blocker) to reverse the attachment of the blocking group and restore the 3'-OH group, the non-catalytic metal ions are added back to the system in preparation for the next cycle, in which the next unincorporable nucleotide is added. Buffer washes are carried out between each reagent addition to reduce background. As mentioned above, the DNA can also be attached directly to the surface of the chamber.

Example 2

FRET-Based SBS with Donor Dye on Polymerase, Acceptor Dye on Terminal Phosphate of Nucleotide Reversible Terminators (NRTs)

Figure 7:
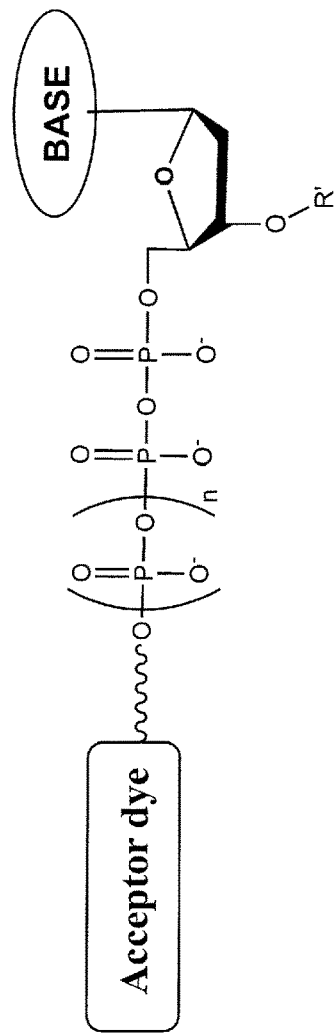
FIG. 7: General structure of fluorescently labeled 3'-reversibly blocked nucleotide with acceptor fluorophore(s) attached at the terminal phosphate.

In this approach, the initial mixture consists of the magnetic bead-bound template or primer DNA, the free primer or template, the donor dye-bearing polymerase, and NRTs with one or two acceptor dyes on the terminal phosphate (FIG. 7). In addition the solution contains non-catalytic metal ions such as $Sr^{++}$ or $Ca^{++}$ (Vander Horn 2014). Briefly, after amplification of DNA on the beads by emulsion PCR or directly on the chamber surface by bridge amplification if the ensemble sequencing format is desired, they are washed to remove $Mg^{++}$ and any other catalytic metal ions. When the beads are deposited onto the surface, $Sr^{++}$ or $Ca^{++}$ is added along with the primer, polymerase and the nucleotides bearing the 3' blocking group and the terminal phosphate-bound acceptor dye(s). After sufficient time to form the ternary complex, acceptor emission measurements are made. Following measurement for as long as needed to obtain a convincing FRET signature, catalytic metals such as $Mg^{+-}$ or $Mn^{++}$ are added to allow incorporation, and after a buffer wash, TCEP is added to remove the blocking group. Finally, $Ca^{++}$ or $Sr^{++}$ is added back to the solution in preparation for the addition of the subsequent nucleotide to the solution for the next cycle of the sequencing process. Non-catalytic metals can also be added before the deblocking step to prevent incorporation of any residual nucleotides in the case of homopolymer stretches, but this is unlikely to be necessary if washes are thorough. The advantages of this method are that it only requires a set of four nucleotides, and that in each round it restores the growing DNA strand to a natural DNA helical state. In the case of single molecule sequencing, instead of using templates amplified on beads, templates may instead be reacted with primers bound directly to the surface of the reaction chamber.

Example 3

Single Molecule Real-Time FRET SBS

Figure 8:
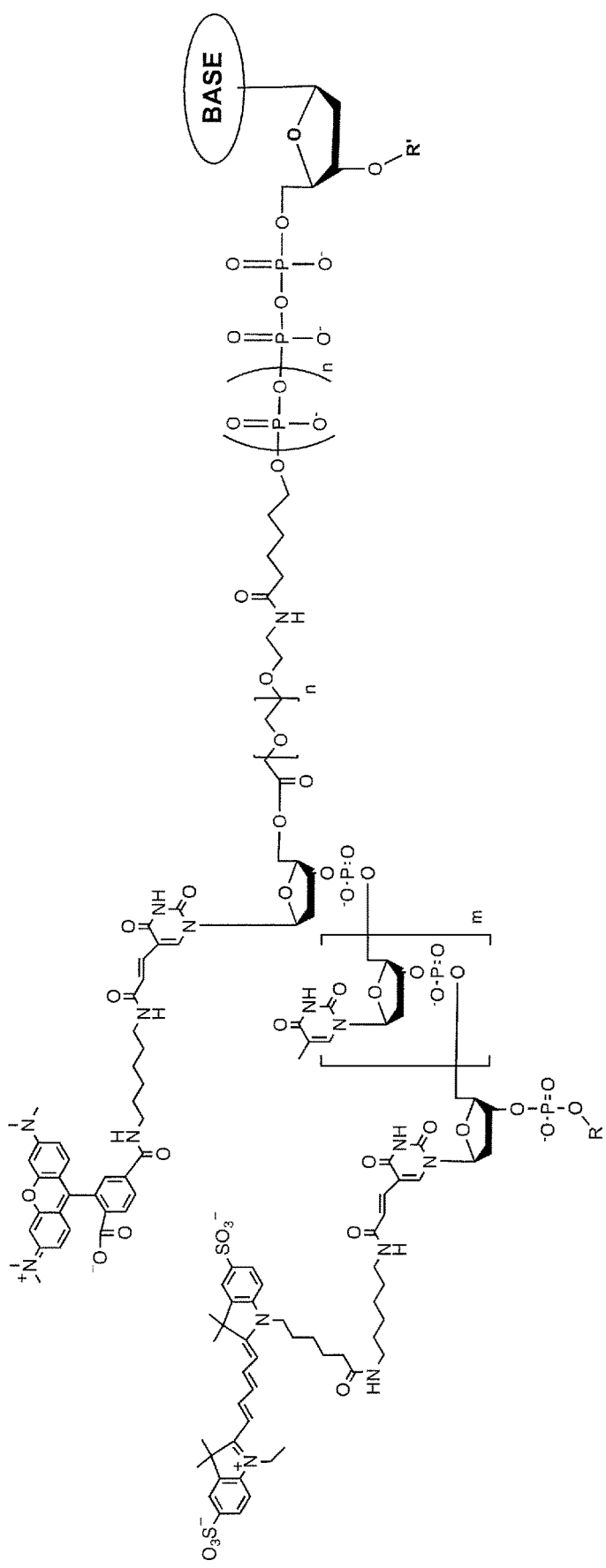
FIG. 8: Example of a combinatorial fluorescence energy transfer label on the terminal phosphate of a 3'-reversibly blocked nucleotide.

In this variant, the polymerase is attached to the magnetic beads, and the template, primer, and nucleotides will be present in the surrounding buffer. Four different nucleotides with acceptor fluorophores are added at the same time, each able to be excited by the donor on the polymerase, but each bearing a different acceptor or FRET pair of acceptors. An example of a combinatorial fluorescent energy transfer tag is shown in FIG. 8. In this 4-color method, continuous fluorescent monitoring is required in order to follow the nucleotide incorporation events in real time. This approach requires the use of a TIRF instrument or other sophisticated imaging device.

REFERENCES

Hung, S-C., et al Cyanine dyes with high absorption cross section as donor chromophores in energy transfer primers. 243, 15-27 (1996).

Turro, N. J., Ramamurthy, V., Scaiano, J. C. Modern Molecular Photochemistry of Organic Molecules, University Science Books, Sausalito, Calif., USA (2010).

Ju, J., et al. Fluorescence energy transfer dye-labeled primers for DNA sequencing and analysis. *Proc. Natl. Acad. Sci. U.S.A.* 92, 4347-4351 (1995).

Nikiforov, T., et al. Conjugates of biomolecules to nanoparticles. U.S. Pat. No. 8,603,792 B2 (2013).

Peng, Y., et al. CdSe/ZnS core shell quantum dots based FRET binary oligonucleotide probes for detection of nucleic acids. *Photochem. Photobiol. Sci.* 11, 881-884 (2012).

Marti, A. A., et al. Inorganic-organic hybrid luminescent binary probe for DNA detection based on spin-forbidden resonance energy transfer. *J. Am. Chem. Soc.,* 129, 8680-8681 (2007).

Tong, A. K., et al. Triple energy transfer in covalently trichromophore-labeled DNA. *J. Am. Chem. Soc.* 123, 12923-12924 (2001).

Upton, T. G., et al. Alpha, beta-difluoromethylene deoxynucleoside 5'-triphosphates: a convenient synthesis of useful probes for DNA polymerase beta structure and function. *Org. Lett.* 11, 1883-1886 (2009).

Guo J, et al. Four-color DNA sequencing with 3'-O-modified nucleotide reversible terminators and chemically cleavable fluorescent dideoxynucleotides. *Proc. Natl. Acad. Sci. U.S.A.* 105, 9145-9150 (2008).

Ju, J., et al. Four-color DNA sequencing by synthesis using cleavable fluorescent nucleotide reversible terminators. *Proc. Natl. Acad. Sci. U.S.A.* 103, 19635-19640 (2006).

Lipshutz, B. H., Harvey, D. F. Hydrolysis of acetals and ketals using LiBF4, *Synth. Commun.* 12, 267-277 (1982).

Ireland, R. E., Varney M. D. Approach to the total synthesis of chlorothricolide: synthesis of (+/−)-19,20-dihydro-24-O-methylchlorothricolide, methyl-ester, ethyl carbonate. *J. Org. Chem.* 51, 635-648 (1986).

Yang, S. G., Park, M. Y., Kim, Y. H. Facile and chemoselective cleavages of allyl ethers utilizing tetrabutylammonium sulfate radical species. *Synlett.* 2002, 492-494 (2002).

Vander Horn, P. B. Nucleotide transient binding for sequencing methods. U.S. Pat. No. 8,632,975 B2 (2014

What is claimed is:

1. A nucleotide analogue having the structure:

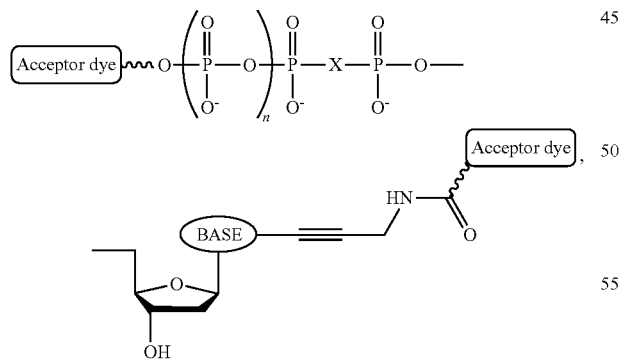

wherein the base is adenine, guanine, cytosine, uracil, thymine, or a derivative thereof, wherein X is $CH_2$, NH, CHF, or $CF_2$, wherein n is 0, 1, 2, 3, or 4, wherein the acceptor dye is 2 or 3 fluorophores.

2. The nucleotide analogue of claim 1, wherein the fluorophore is a cyanine dye, a rhodamine dye, fluorescein, acridine, coumarin, Texas Red dye, BODIPY, GFP, rhodol, ROX, resorfuin, Alexa Flour, Tokyo Green, N,N,N',N'-tetramethyl-6-carboxyrhodamine, or a plurality of any of the foregoing.

3. A method for determining the identity of a nucleotide in a single-stranded DNA comprising:
a) contacting a composition comprising a single-stranded DNA having a primer hybridized to a portion thereof, a nucleotide polymerase, and a nucleotide analogue having the structure:

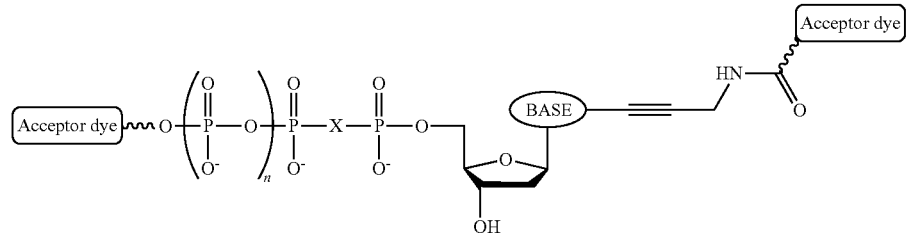
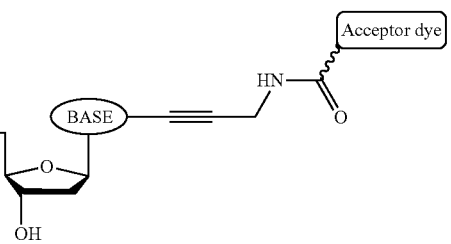

wherein the base is A, C, G, T, or U, or analogues thereof, wherein X is $CH_2$, NH, CHF, or $CF_2$, wherein n is 0, 1, 2, 3, or 4, wherein the acceptor dye is one or more fluorophores, and wherein X prevents a nucleotide polymerase from hydrolyzing the bond between the α and β phosphates, under conditions permitting the nucleotide polymerase to form a ternary complex with the single-stranded DNA, primer, and the nucleotide analogue if the nucleotide analogue has a base that is complementary to a nucleotide residue of the single-stranded DNA which is immediately 5' to a nucleoside residue of the single-stranded DNA hybridized to the 3' terminal nucleotide residue of the primer, wherein the DNA polymerase has attached, incorporated, and/or conjugated fluorescence donor molecules, wherein the donor molecules are Förster Resonance Energy Transfer (FRET) donors, and the acceptor dyes on the nucleotide analogue are corresponding FRET acceptors, wherein if the base of the nucleotide analogue is not complementary to the nucleotide residue of the single-stranded DNA which is immediately 5' to the nucleoside residue of the single-stranded DNA hybridized to the 3' terminal nucleotide residue of the primer, iteratively repeating the contacting with a different nucleotide analogue until a nucleotide analogue is complementary to the nucleotide residue of the single-stranded DNA which is immediately 5' to the nucleoside residue of the single-stranded DNA hybridized to the 3' terminal nucleotide residue of the primer, thus forming a ternary complex, with the proviso that (i) the type of base on each nucleotide analogue is different from the type of base on each of the other nucleotide analogues, and (ii) the acceptor dyes of each nucleotide analogue fluorophore has a predetermined fluorescent wavelength emission;

b) exciting the DNA polymerase donor fluorescent molecules using an appropriate spectral emission, thereby causing the corresponding FRET acceptors, which are the acceptor dye organic fluorophores attached to nucleotide analogue in the ternary complex, to generate the predetermined fluorescent wavelength emission, and thereby determine the identity of the nucleotide analogue.

4. A method for determining the nucleotide sequence of a single-stranded DNA comprising:

a) contacting the single-stranded DNA which has a primer hybridized to a portion thereof, a nucleotide polymerase, and a nucleotide analogue having the structure:

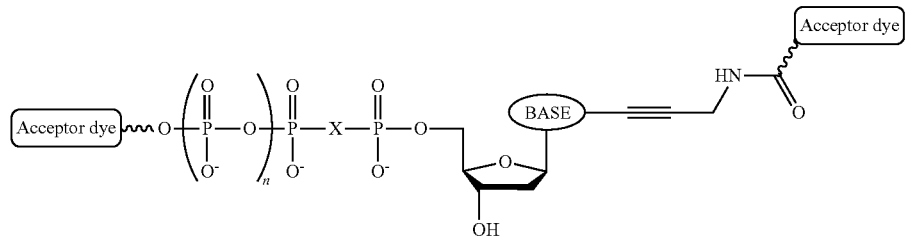

wherein the base is A, G, C, I, or U, or analogues thereof, wherein X is $CH_2$, NH, CHF, or $CF_2$, wherein n is 0, 1, 2, 3, or 4, wherein the acceptor dye is one or more fluorophores, and wherein X prevents a nucleotide polymerase from hydrolyzing the bond between the α and β phosphates wherein the nucleotide polymerase has attached, incorporated, and/or conjugated fluorescence donor molecules, wherein the donor molecules are Förster Resonance Energy Transfer (FRET) donors, and the acceptor dyes on the nucleotide analogue are corresponding FRET acceptors, under conditions permitting the DNA polymerase to form a ternary complex with the single-stranded DNA, primer, and nucleotide analogue if the analogue has a base that is complementary to a nucleotide residue of the single-stranded DNA which is immediately 5' to a nucleoside residue of the single-stranded DNA hybridized to the 3' terminal nucleotide residue of the primer, and if the base of the nucleotide analogue is not complementary to the nucleotide residue of the single-stranded DNA which is immediately 5' to the nucleoside residue of the single-stranded DNA hybridized to the 3' terminal nucleotide residue of the primer, iteratively repeating the contacting with a different nucleotide analogue until the analogue is complementary to the nucleotide residue of the single-stranded DNA which is immediately 5' to the nucleotide residue of the single-stranded DNA hybridized to the 3' terminal nucleotide residue of the primer, thus forming a ternary complex, with the proviso that (i) the type of base on each nucleotide analogue is different from the type of base on each of the other nucleotide analogues, and (ii) the fluorophore of each nucleotide analogue has a predetermined fluorescent wavelength emission;

b) exciting the nucleotide polymerase fluorescence donor molecules using an appropriate spectral emission, thereby causing the corresponding FRET acceptors, which are the acceptor dye organic fluorophores attached to the nucleotide analogue in the ternary complex, to generate the predetermined fluorescent wavelength emission, and thereby determine the identity of the nucleotide analogue;

c) contact the ternary complex with 3'-O blocked nucleotide reversible terminators under conditions permitting the nucleotide polymerase to catalyze incorporation onto the primer of a 3'O-blocked nucleotide reversible terminator complementary to a nucleotide residue of the single-stranded DNA which is immediately 5' to a nucleotide residue of the single-stranded DNA hybridized to the 3' terminal nucleotide residue of the primer, thereby replacing the nucleotide analogue in the ternary complex, wherein the 3'-O blocked nucleotide reversible terminators have the structure:

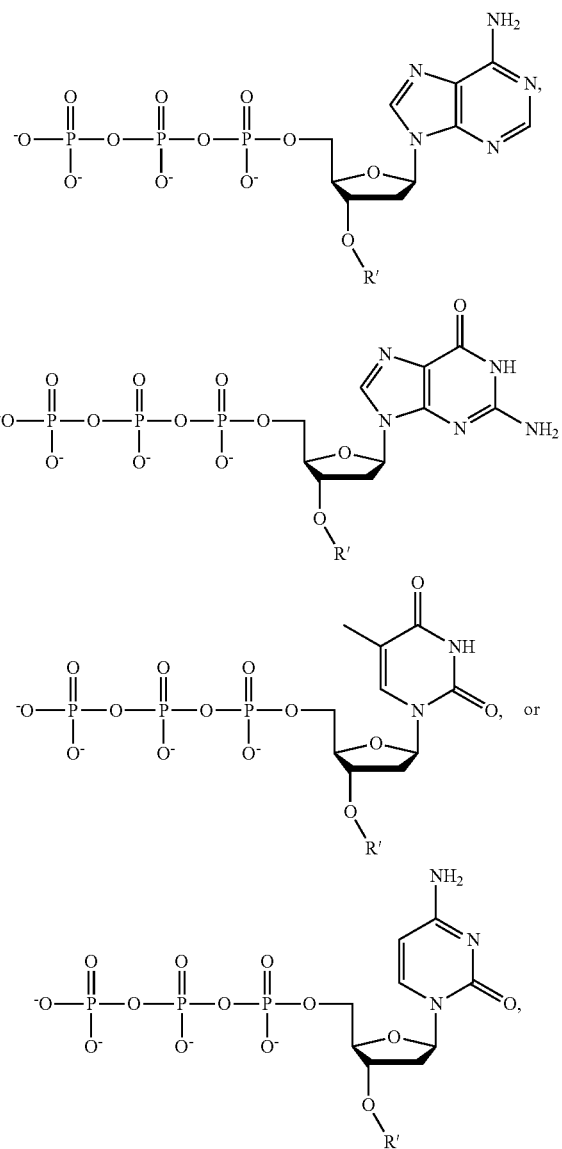

wherein R' is a cleavable linker bound to a blocking moiety, and wherein cleaving the linker results in a 3'-OH;
d) cleaving the linker bound to the blocking moiety of the incorporated 3'-O blocked nucleotide reversible terminator, thereby resulting in a 3'-OH;
e) iteratively performing steps a) through d) for each nucleotide residue of the single-stranded DNA to be sequenced so as to thereby determine the sequence of the single-stranded DNA.

5. A method for determining the nucleotide sequence of a single-stranded DNA comprising:
a) contacting a composition comprising a single-stranded DNA which has a primer hybridized to a portion thereof, a nucleotide polymerase, and four nucleotide analogues having the structure:

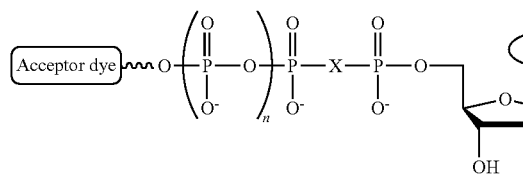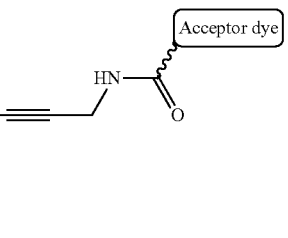

wherein the base is adenine, guanine, cytosine, uracil, thymine, or analogues thereof, wherein n is 0, 1, 2, 3, or 4, wherein the acceptor dye is one or more fluorophores, and wherein X prevents a nucleotide polymerase from hydrolyzing the bond between the α and β phosphates,
wherein the nucleotide polymerase has attached, incorporated, and/or conjugated fluorescence donor molecules, wherein the donor molecules are Förster Resonance Energy Transfer (FRET) donors, and the acceptor dyes on the nucleotide analogue are corresponding FRET acceptors,
wherein (i) the type of base on each analogue is different from the type of base on each of the other three analogues, (ii) the fluorophores of each nucleotide analogue have a unique predetermined fluorescent wavelength emission that corresponds to type of base, and (iii) the fluorophores of each analogue are FRET acceptors that are excited by same donor fluorescence molecules in the nucleotide polymerase;
under conditions permitting the nucleotide polymerase to form a ternary complex with the single-stranded DNA, primer, and a nucleotide analogue wherein the nucleotide analogue has a base that is complementary to a nucleotide residue of the single-stranded DNA which is immediately 5' to a nucleoside residue of the single-stranded DNA hybridized to the 3' terminal nucleotide residue of the primer,
and if the base of the nucleotide analogue is not complementary to the nucleotide residue of the single-stranded DNA which is immediately 5' to the nucleoside residue of the single-stranded DNA hybridized to the 3' terminal nucleotide residue of the primer, iteratively repeating the contacting with a different nucleotide analogue until the analogue is complementary to the nucleotide residue of the single-stranded DNA which is immediately 5' to the nucleotide residue of the single-stranded DNA hybridized to the 3' terminal nucleotide residue of the primer, thus forming a ternary complex;

b) exciting the nucleotide polymerase fluorescent donor molecules using an appropriate spectral emission, thereby causing the corresponding FRET acceptors, which are the acceptor dye fluorophores attached to the nucleotide analogue in the ternary complex, to generate the unique predetermined fluorescent wavelength emission, and thereby determine the identity of the nucleotide analogue;

c) contact the ternary complex with 3'-O blocked nucleotide reversible terminators under conditions permitting the nucleotide polymerase to catalyze incorporation onto the primer of a 3'O-blocked nucleotide reversible terminator complementary to a nucleotide residue of the single-stranded DNA which is immediately 5' to a nucleotide residue of the single-stranded DNA hybridized to the 3' terminal nucleotide residue of the primer, thereby replacing the nucleotide analogue in the ternary complex, wherein the 3'-O blocked nucleotide reversible terminators have the structure:

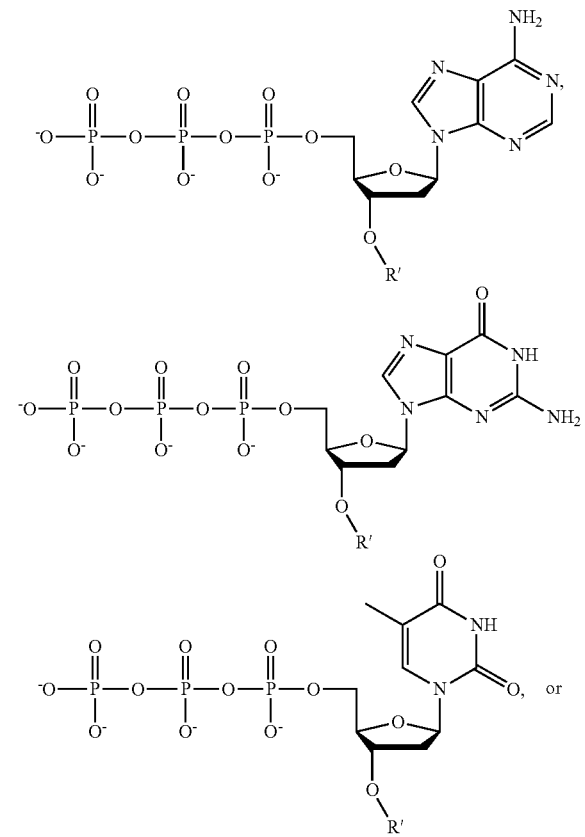

-continued

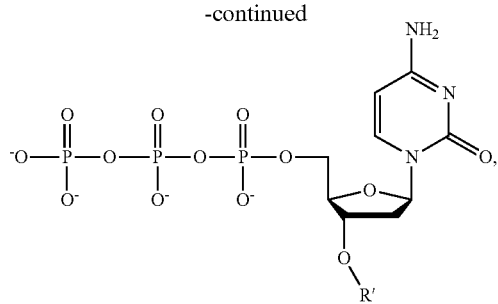

wherein R' is a cleavable linker bound to a blocking moiety, and wherein cleaving the linker results in a 3'-OH;

d) cleaving the linker bound to the blocking moiety of the incorporated 3'-O blocked nucleotide reversible terminator, thereby resulting in a 3'-OH;

e) iteratively performing steps a) through d) for each nucleotide residue of the single-stranded DNA to be sequenced so as to thereby determine the sequence of the single-stranded DNA.

6. The method of claim 3, wherein the acceptor dyes comprise 1, 2, or 3 organic fluorophores.

7. The method of claim 3, wherein the organic fluorophore is a cyanine dye, a rhodamine dye, fluorescein, acridine, coumarin, Texas Red dye, BODIPY, GFP, rhodol, ROX, resorfuin, Alexa Flour, a quantum dot, Tokyo Green, or N,N,N',N'-tetramethyl-6-carboxyrhodamine.

8. The method of claim 3, wherein the nucleotide polymerase fluorescence donor molecules are one or more of a cyanine dye, a rhodamine dye, fluorescein, acridine, coumarin, Texas Red dye, BODIPY, GFP, rhodol, ROX, resorfuin, Alexa Flour, a quantum dot, Tokyo Green, an Ru(II) polypyridyl complex, N,N,N',N'-tetramethyl-6-carboxyrhodamine, or any derivative thereof.

9. The method of claim 3, wherein the primer, single-stranded DNA, or nucleotide polymerase are bound to a magnetic bead or the surface of a fluidic chamber.

10. The method of claim 9, wherein the primer, single-stranded DNA, or nucleotide polymerase bound to the magnetic bead or surface are modified with one of amino, sulfhydryl, or biotin moieties.

11. The method of claim 3, wherein the method is performed simultaneously on a plurality of single-stranded DNAs.

12. The method of claim 3, wherein prior to step a), the single-stranded DNA is amplified using emulsion PCR thereby resulting in a plurality of copies of the single-stranded DNA.

13. The method of claim 12, wherein prior to step a), several copies of the single-stranded DNA are created on a bead using emulsion PCR.

14. The method of claim 3, wherein the single-stranded DNA is bound to a surface and remains there during the iterative process.

15. The method of claim 3, wherein when the ternary complex is formed, the nucleotide polymerase fluorescence donor molecule and the nucleotide analogue acceptor fluorophore are less than 10 nm from each other.

16. The method of claim 15, wherein the DNA polymerase fluorescence donor molecule and the nucleotide analogue acceptor fluorophore are between 2 nm-4 nm from each other.

17. The method of claim 3, wherein time-gated luminescence detection techniques are used to detect the nucleotide analogue acceptor emission signal.

18. The method of claim 3, where the DNA polymerase is a mutant *Geobacillus kaustophilus* DNA polymerase I or Phi29 DNA polymerase.

19. The method of claim 18, wherein the polymerase has pairs of cysteines in antipodal locations wherein the fluorescence donor molecules are attached.

20. A nucleotide analogue having the structure:

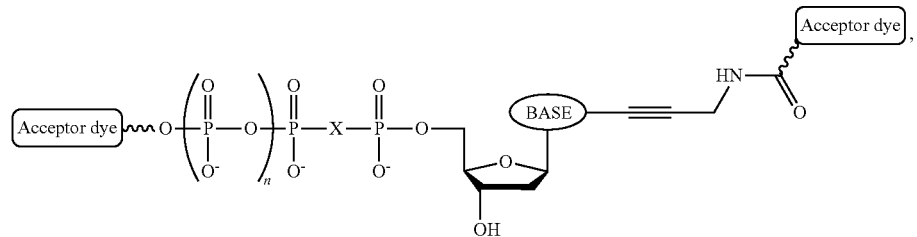

wherein the base is adenine, guanine, cytosine, uracil, thymine, or a derivative thereof, wherein X is $CH_2$, NH, CHF, or $CF_2$, wherein n is 0, 1, 2, 3, or 4, wherein the acceptor dye is a fluorophore.

* * * * *